(12) United States Patent
Brandt

(10) Patent No.: US 12,138,439 B2
(45) Date of Patent: *Nov. 12, 2024

(54) INTRAVASCULAR BLOOD PUMPS WITH STRUTS AND METHODS OF USE AND MANUFACTURE

(71) Applicant: Shifamed Holdings, LLC, Campbell, CA (US)

(72) Inventor: Brian D. Brandt, Morgan Hill, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/193,338

(22) Filed: Mar. 30, 2023

(65) Prior Publication Data

US 2023/0264012 A1    Aug. 24, 2023

Related U.S. Application Data

(63) Continuation of application No. 16/936,160, filed on Jul. 22, 2020, now Pat. No. 11,654,275.

(60) Provisional application No. 62/877,154, filed on Jul. 22, 2019.

(51) Int. Cl.
| | |
|---|---|
| *A61M 60/216* | (2021.01) |
| *A61M 60/13* | (2021.01) |
| *A61M 60/268* | (2021.01) |
| *A61M 60/414* | (2021.01) |
| *A61M 60/808* | (2021.01) |
| *A61M 60/857* | (2021.01) |

(52) U.S. Cl.
CPC ........ *A61M 60/857* (2021.01); *A61M 60/268* (2021.01); *A61M 60/414* (2021.01); *A61M 2205/0266* (2013.01); *A61M 2207/00* (2013.01)

(58) Field of Classification Search
CPC .............. A61M 2207/00; A61M 60/13; A61M 60/237; A61M 60/414; A61M 60/808; A61M 60/857; A61M 2205/0266; A61M 2230/30; A61M 60/268; A61M 60/804; A61M 60/81; A61M 60/816; A61M 60/865; A61M 60/139; A61M 60/174; A61M 60/216; A61M 60/295
See application file for complete search history.

(56) References Cited

U.S. PATENT DOCUMENTS

| | | | |
|---|---|---|---|
| 11,654,275 B2 * | 5/2023 | Brandt ................ | A61M 60/808 600/16 |
| 2017/0087288 A1 | 3/2017 | Gross-Hardt et al. | |
| 2018/0326132 A1 | 11/2018 | Maimon et al. | |
| 2021/0008261 A1 * | 1/2021 | Calomeni .......... | A61M 60/174 |

* cited by examiner

*Primary Examiner* — Jon Eric C Morales
(74) *Attorney, Agent, or Firm* — Shay Glenn LLP

(57) ABSTRACT

Catheter blood pumps that include an expandable pump portion, which include an expandable impeller housing. The housings include an expandable blood conduit that defines a blood lumen, and one or more pluralities of expandable struts extending axially from an end region of the expandable blood conduit. At least one of the pluralities of struts are non-unitary with a blood conduit at the end region.

12 Claims, 18 Drawing Sheets

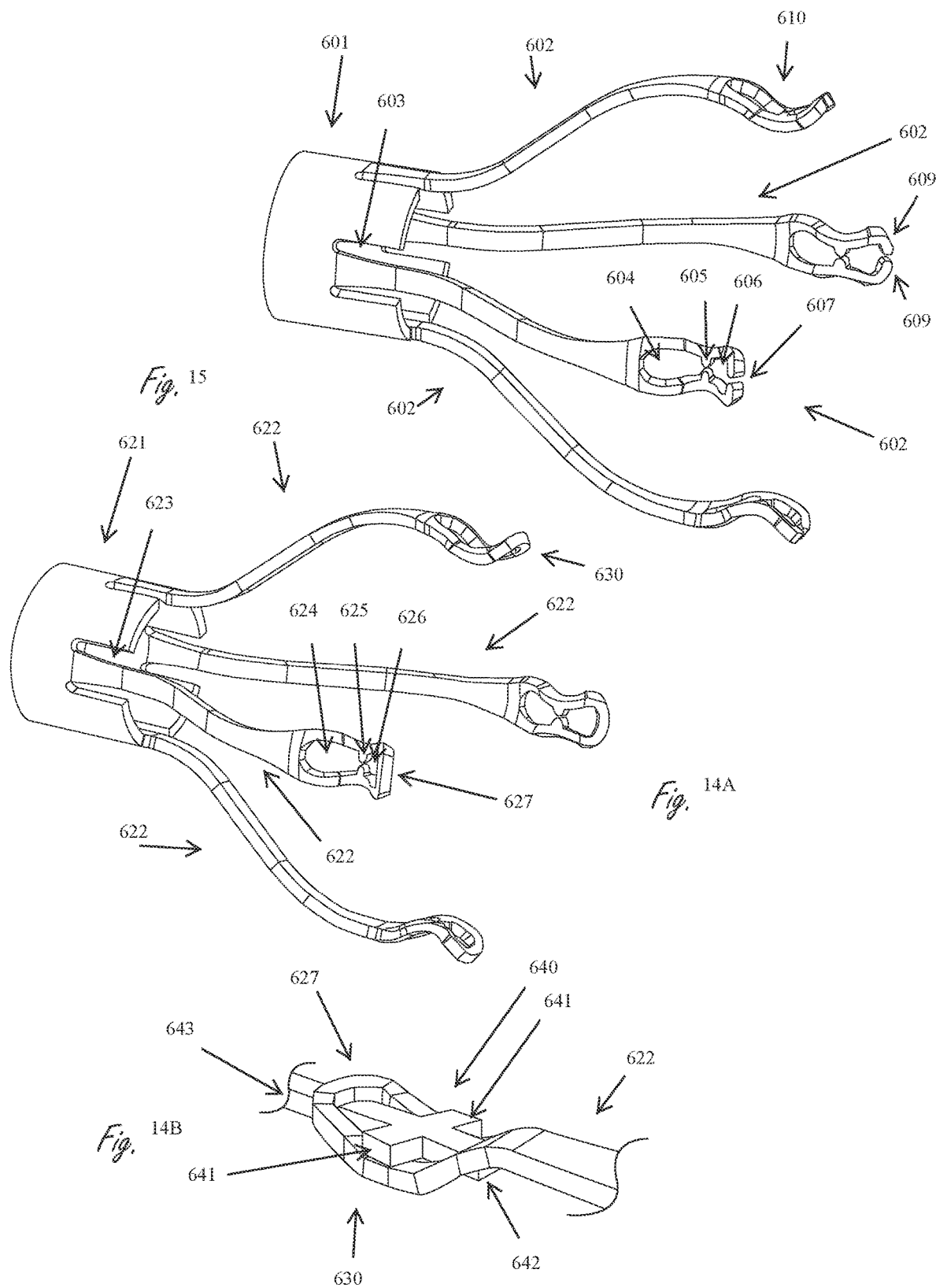

ABSTRACT# INTRAVASCULAR BLOOD PUMPS WITH STRUTS AND METHODS OF USE AND MANUFACTURE

CROSS REFERENCE TO RELATED APPLICATIONS

This application is a continuation of U.S. application Ser. No. 16/936,160, filed Jul. 22, 2020, which claims priority to U.S. Provisional Application No. 62/877,154, filed Jul. 22, 2019, each of which are incorporated by reference herein in its entirety for all purposes.

This application is related to and incorporates by reference herein for all purposes the disclosures of the following applications: WO2018/226991, WO2019/094963, WO2019/152875, and WO2020/028537.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions, and one of the functions is to attempt to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular support device.

There is a need to provide additional improvements to the field of ventricular support devices and similar blood pumps for treating compromised cardiac blood flow.

SUMMARY OF THE DISCLOSURE

This disclosure is related to pump portions of catheter blood pumps, and their use and manufacture.

One aspect of the disclosure is a catheter blood pump, comprising: an expandable pump portion extending distally from an elongate shaft. The pump portion includes an expandable impeller housing. The housing includes an expandable blood conduit defining a blood lumen, and a plurality of struts coupled to and extending axially from an end region of the expandable blood conduit, where the plurality of struts non-unitary with the expanable blood conduit. The pump portion also includes one or more expandable impellers.

In this aspect the plurality of expandable struts may be coupled to an expandable scaffold at the end region of the expandable blood conduit.

In this aspect the plurality of expandable struts may be disposed at an outflow of the pump portion. In this aspect the plurality of expandable struts may be disposed at an inflow of the pump portion.

In this aspect the plurality of expandable struts may be proximal relative to a proximal end of the expanable blood conduit. The plurality of expandable struts may be disposed at an inflow of the pump portion.

In this aspect the plurality of expandable struts may be disposed distal relative to a distal end of the expanable blood conduit.

In this aspect the blood pump may further comprise a second plurality of struts extending axially from a second end region of the expandable blood conduit. The second plurality of struts may be unitary or non-unitary with the scaffold. In this aspect the scaffold may extend from the end region to a second end region. In this aspect the scaffold may be continuous from the end region to a second end region. In this aspect the scaffold may include one or more discontinuities between the end region and the second end region.

In this aspect the scaffold may include first and second scaffold sections axially spaced apart. First and second scaffold sections may be disposed at first and second impeller regions. In this aspect the blood conduit may include a central region in between first and second scaffold sections, wherein the central region is void of a scaffold.

In this aspect the plurality of expandable struts may be disposed at an outflow of the pump portion and a second plurality of expandable struts may be disposed at an inflow of the pump portion. The plurality of expandable struts may be disposed at an inflow of the pump portion and a second plurality of expandable struts may be disposed at an outflow of the pump portion.

In this aspect the plurality of expandable struts may have a dimension that is different than a dimension of an end region of the scaffold. In some examples the struts have a radial thickness greater than a radial thickness of the scaffold in the end region. In some examples the struts have a width greater than a width of the scaffold in the end region.

In this aspect the plurality of expandable struts and the scaffold comprise the same material, such as a metallic alloy such as nitinol.

In this aspect the plurality of expandable struts extend from a common strut hub, wherein a strut hub and the plurality of expandable struts may be unitary.

In this aspect each of the plurality of struts may have a stiffness that is greater than a region of the scaffold to which it is coupled.

In this aspect the expandable blood conduit may further comprises a membrane secured to the scaffold. A membrane herein may comprise one or more polymeric layers.

In this aspect the plurality of struts may each have a first securing member secured to a second securing member of the scaffold. A first securing member may be disposed at an end region of the strut. A first securing member may comprise a bend in the strut. A first securing member may include one or more projections that project away from an elongate strut body. A first securing member may have a T configuration. A first securing member may have a hook configuration. A second securing member may comprise a bend in the scaffold. A second securing member may have a valley configuration in the scaffold. A first securing member may comprise an opening in the strut.

In this aspect the plurality of struts may each have closed free ends.

In this aspect the plurality of struts have each have open free ends, optionally including a plurality of fingers that define the open end.

In this aspect first securing members may comprise one or more projections extending from side arms of the strut, the projections optionally partially defining an opening in the strut.

In this aspect first securing members may have a valley configuration comprising a bend.

In this aspect a second securing member may comprise an elongate body that extends at least partially within a strut opening.

In this aspect a first securing member and a second securing member may be separately and together sized, positioned, and configured to engage one another such that one or more surfaces on each interact and cause a resistance to movement of one or both of the first and securing members in at least one direction.

In this aspect the coupling between each of the plurality of struts and the end region comprises a weld.

In this aspect the plurality of struts includes from at least two to ten struts, optionally two to eight struts.

As used herein, a strut is generally described as a structure extending away from a structure to which it is coupled. Struts may comprise a main body, such as extending from a hub, and may become branched, such that there are more than one strut main bodies. The branched regions of the strut are generally considered part of the strut.

In this aspect any of the blood pumps may be manufactured, wherein the manufacture includes coupling each of the plurality of struts to the end region of the blood conduit, and optionally to a scaffold of the blood conduit. Scaffolds herein may be formed from a variety of materials or combinations thereof, such a metals, alloys, polymers, etc.

One aspect of the disclosure is a method of manufacturing a pump portion of a catheter blood pump, such as any of the pump portions herein.

This aspect may include coupling each of a plurality of struts to an end region of an expandable scaffold, the expandable scaffold part of an expandable blood conduit that defines a blood lumen, and positioning one or more collapible impellers at least partially within the blood lumen.

In this aspect, the method may further comprise securing a membrane to the expandable scaffold prior in time to the coupling step. Securing a membrane to the expandable scaffold may be performed on a mandrel.

In this aspect, the method may further comprise coupling each of a second plurality of struts to a second end region of an expandable scaffold.

In this aspect, the coupling step may comprise coupling each of the plurality of struts that extend from a unitary hub to the end region of the expandable scaffold.

In this aspect, positioning the one or more impellers may occur prior in time to coupling each of the plurality of struts to the end region of the expandable scaffold.

In this aspect, the coupling step may comprise coupling each of a plurality of struts to an end region of an expandable scaffold, wherein the expandable scaffold extends along the blood conduit.

In this aspect, the coupling step may comprise coupling each of a plurality of struts to a first scaffold section that is axially spaced from a second scaffold section. The method may further comprise coupling each of a second plurality of struts to the second scaffold section. In this aspect, coupling each of a second plurality of struts to a second end region of an expandable scaffold may comprise coupling each of the second plurality of struts to a second scaffold section of the expandable scaffold.

In this aspect, coupling each of a plurality of struts to an end region of an expandable scaffold may comprise coupling each of a plurality of struts to an end region of an expandable scaffold from which a second plurality of struts extend, wherein the second plurality of struts are unitary with the scaffold. Second plurality of struts may be unitary with a second scaffold section of the scaffold.

BRIEF DESCRIPTION OF THE DRAWINGS

FIG. 14A illustrates an exemplary strut assembly including a plurality of struts.

FIG. 14B illustrates an exemplary coupling of a strut and an end region of an expandable scaffold.

FIG. 15 illustrates an exemplary strut assembly including a plurality of struts.

DETAILED DESCRIPTION

The present disclosure is related to medical devices, systems, and methods of use and manufacture. Medical devices herein may include a distal pump portion (which may also be referred to herein as a working portion) adapted to be disposed within a physiologic vessel, wherein the distal pump portion includes one or more components that act upon fluid. For example, pump portions herein may include one or more rotating members that when rotated, can facilitate the movement of a fluid such as blood.

Any of the disclosure herein relating to an aspect of a system, device, or method of use can be incorporated with any other suitable disclosure herein. For example, a figure describing only one aspect of a device or method can be included with other embodiments even if that is not specifically stated in a description of one or both parts of the disclosure. It is thus understood that combinations of different portions of this disclosure are included herein.

Figure 1:
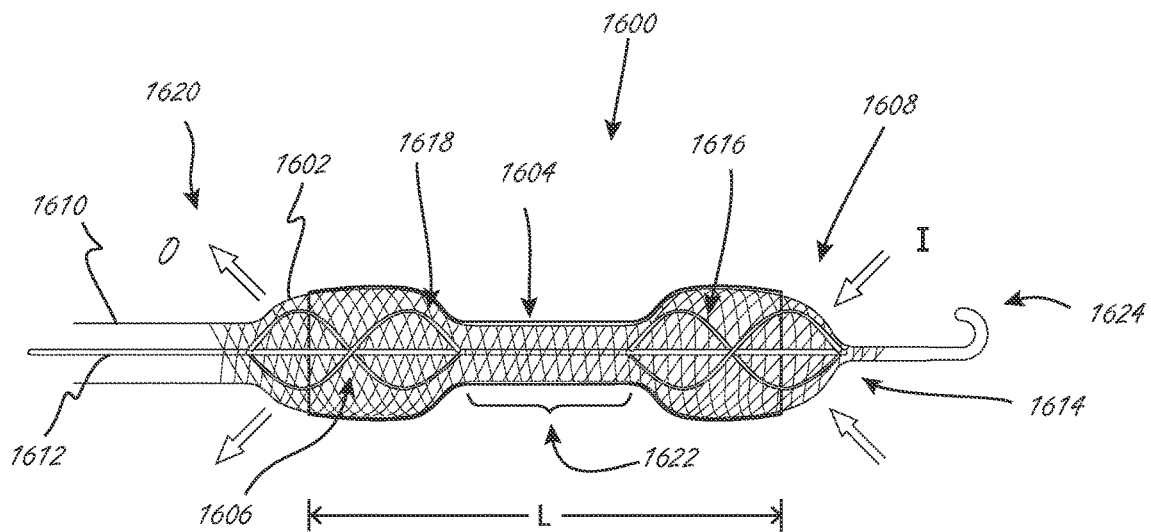
FIG. 1 is a side view of an exemplary expandable pump portion that includes an expandable impeller housing, blood conduit and a plurality of impellers.

FIG. 1 is a side view illustrating a distal portion of an exemplary catheter blood pump, including pump portion 1600, wherein pump portion 1600 includes proximal impeller 1606 and distal impeller 1616, both of which are in operable communication with drive cable 1612. Pump portion 1600 is in an expanded configuration in FIG. 1, but is adapted to be collapsed to a delivery configuration so that it can be delivered with a lower profile. The impellers can be attached to drive mechanism 1612 (e.g., a drive cable). Drive mechanism 1612 is in operable communication with an external motor, not shown, and extends through elongate shaft 1610. The phrases "pump portion" and "working portion" (or derivatives thereof) may be used herein interchangeably unless indicated to the contrary. For example without limitation, "pump portion" 1600 can also be referred to herein as a "working portion."

Pump portion 1600 also includes expandable member or expandable scaffold 1602, which in this embodiment has a proximal end 1620 that extends further proximally than a proximal end of proximal impeller 1606, and a distal end 1608 that extends further distally than a distal end 1614 of distal impeller 1616. Expandable members may also be referred to as expandable scaffolds herein. Expandable scaffold 1602 is disposed radially outside of the impellers along the axial length of the impellers. Expandable scaffold 1602 can be constructed in a manner and made from materials similar to many types of expandable structures that are known in the medical arts to be able to be collapsed and expanded, examples of which are provided herein. Examples of suitable materials include, but are not limited to, polyurethane and polyurethane elastomers.

Pump portion 1600 also includes blood conduit 1604, which is coupled to expandable member 1602, has a length L, and extends axially between the impellers. Conduit 1604 creates and provides a fluid lumen between the two impellers. When in use, fluid move through the lumen provided by conduit 1604. The conduits herein are non-permeable, or they can be semipermeable, or even porous as long as they can still define a lumen. The conduits herein are also flexible, unless it is otherwise indicated. The conduits herein extend completely around (i.e., 360 degrees) at least a portion of the pump portion. In pump portion 1600, conduit extends completely around expandable member 1602, but does not extend all the way to the proximal end 1602 or distal end 1608 of expandable member 1602. The structure of the expandable member creates at least one inlet aperture to allow for inflow "I," and at least one outflow aperture to allow for outflow "O." Conduit 1604 improves impeller pumping dynamics, compared to those that working portion 1600 would have without the conduit.

Expandable member 1602 may have a variety of constructions, and made from a variety of materials. For example, expandable member 1602 may be formed similar to expandable stents or stent-like devices, or any other example provided herein. For example without limitation, expandable member 1602 could have an open-braided construction, such as a 24-end braid, although more or fewer braid wires could be used. Exemplary materials for the expandable member as well as the struts herein include nitinol, cobalt alloys, and polymers, although other materials could be used. Expandable member 1602 has an expanded configuration, as shown, in which the outer dimension (measured orthogonally relative a longitudinal axis of the working portion) of the expandable member is greater in at least a region where it is disposed radially outside of the impellers than in a central region 1622 of the expandable member that extends axially between the impeller. Drive mechanism 1612 is co-axial with the longitudinal axis in this embodiment. In use, the central region can be placed across a valve, such as an aortic valve. In some embodiments, expandable member 1602 is adapted and constructed to expand to an outermost dimension of 12-24F (4.0-8.0 mm) where the impellers are axially within the expandable member, and to an outermost dimension of 10-20F (3.3-6.7 mm) in central region 1622 between the impellers. The smaller central region outer dimension can reduce forces acting on the valve, which can reduce or minimize damage to the valve. The larger dimensions of the expandable member in the regions of the impellers can help stabilize the working portion axially when in use. Expandable member 1602 has a general dumbbell configuration. Expandable member 1602 has an outer configuration that tapers as it transitions from the impeller regions to central region 1622, and again tapers at the distal and proximal ends of expandable member 1602.

Expandable member 1602 has a proximal end 1620 that is coupled to shaft 1610, and a distal end 1608 that is coupled to distal tip 1624. The impellers and drive mechanism 1612 rotate within the expandable member and conduit assembly. Drive mechanism 1612 is axially stabilized with respect to distal tip 1624, but is free to rotate with respect to tip 1624.

In some embodiments, expandable member 1602 can be collapsed by pulling tension from end-to-end on the expandable member. This may include linear motion (such as, for example without limitation, 5-20 mm of travel) to axially extend expandable member 1602 to a collapsed configuration with collapsed outer dimension(s). Expandable member 1602 can also be collapsed by pushing an outer shaft such as a sheath over the expandable member/conduit assembly, causing the expandable member and conduit to collapse towards their collapsed delivery configuration.

Impellers 1606 and 1616 are also adapted and constructed such that one or more blades will stretch or radially compress to a reduced outermost dimension (measured orthogonally to the longitudinal axis of the working portion). For example without limitation, any of the impellers herein can include one or more blades made from a plastic formulation with spring characteristics, such as any of the impellers described in U.S. Pat. No. 7,393,181, the disclosure of which is incorporated by reference herein for all purposes and can be incorporated into embodiments herein unless this disclosure indicates to the contrary. Alternatively, for example, one or more collapsible impellers can comprise a superelastic wire frame, with polymer or other material that acts as a webbing across the wire frame, such as those described in U.S. Pat. No. 6,533,716, the disclosure of which is incorporated by reference herein for all purposes.

The inflow and/or outflow configurations of working portion 1600 can be mostly axial in nature.

Exemplary sheathing and unsheathing techniques and concepts to collapse and expand medical devices are known, such as, for example, those described and shown in U.S. Pat. No. 7,841,976 or U.S. Pat. No. 8,052,749, the disclosures of which are incorporated by reference herein.

Figure 2:
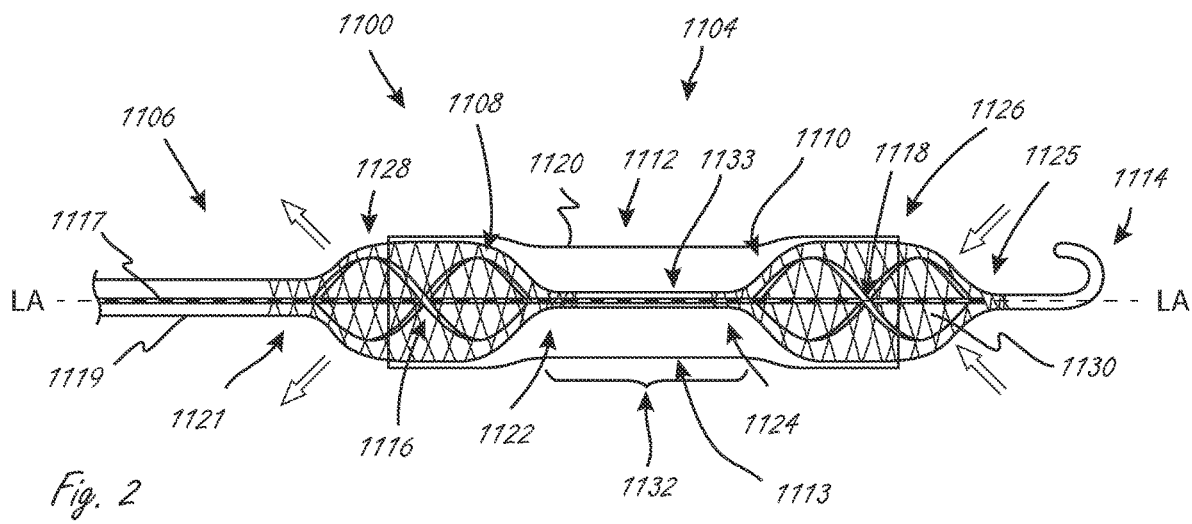
FIG. 2 is a side view of an exemplary expandable pump portion that includes an expandable impeller housing, a blood conduit, a plurality of impellers, and a plurality of expandable scaffolds sections or support members.

FIG. 2 is a side view illustrating a deployed configuration (shown extracorporally) of a distal portion of an exemplary embodiment of a catheter blood pump. Exemplary blood pump 1100 includes working portion 1104 (which as set forth herein may also be referred to herein as a pump portion) and an elongate portion 1106 extending from working portion 1104. Elongate portion 1106 can extend to a more proximal region of the system, not shown for clarity, and that can include, for example, a motor. Working portion 1104 includes first expandable scaffold or member 1108 and second expandable scaffold or member 1110, axially spaced apart along a longitudinal axis LA of working portion 1104. First scaffold 1108 and second scaffold 1110 (and any other separate scaffolds herein) may also be referenced as part of a common scaffold and referred to herein as scaffold sections. Spaced axially in this context refers to the entire first expandable member being axially spaced from the entire second expandable member along a longitudinal axis LA of working portion 1104. A first end 1122 of first expandable member 1108 is axially spaced from a first end 1124 of second expandable member 1110.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in 6,533,716, which is described as a self-expanding metal endoprosthetic material. For example, without limitation, one or both of the expandable members can have a braided construction or can be at least partially formed by laser cutting a tubular element.

Working portion 1104 also includes blood conduit 1112 that is coupled to first expandable member 1108 and to second expandable member 1110, and extends axially in between first expandable member 1108 and second expandable member 1110 in the deployed configuration. A central region 1113 of conduit 1112 spans an axial distance 1132 where the working portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a blood conduit being coupled to an expandable scaffold or member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations.

Any of the blood conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as working portion 1104 is deployed towards the configuration shown in FIG. 2. The conduit may be stretched tightly between the expandable members in some embodiments. The conduit may alternatively be designed with a looseness that causes a greater degree of compliance. This can be desirable when the working portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the blood conduits herein, or at least a portion of the conduit, can be impermeable to blood. In FIG. 2, working portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable scaffolds or members help maintain the blood conduit in an open configuration to create the lumen, while each also creates a working environment for an impeller, described below. Each of the expandable scaffolds, when in the deployed configuration, is maintained in a spaced relationship relative to a respective impeller, which allows the impeller to rotate within the expandable member without contacting the expandable member. Working portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the working portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and working portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Working portion 1104 is adapted and configured to be collapsed to a smaller profile than its deployed configuration (which is shown in FIG. 2). This allows it to be delivered using a lower profile delivery device (smaller French size) than would be required if none of working portion 1104 was collapsible. Even if not specifically stated herein, any of the expandable members and impellers may be adapted and configured to be collapsible to some extent to a smaller delivery configuration.

The working portions herein can be collapsed to a collapsed delivery configuration using conventional techniques, such as with an outer sheath that is movable relative to the working portion (e.g., by axially moving one or both of the sheath and working portion). For example without limitation, any of the systems, devices, or methods shown in the following references may be used to facilitate the collapse of a working portions herein: U.S. Pat. No. 7,841,976 or U.S. Pat. No. 8,052,749, the disclosures of which are incorporated by reference herein for all purposes.

Figure 3A:
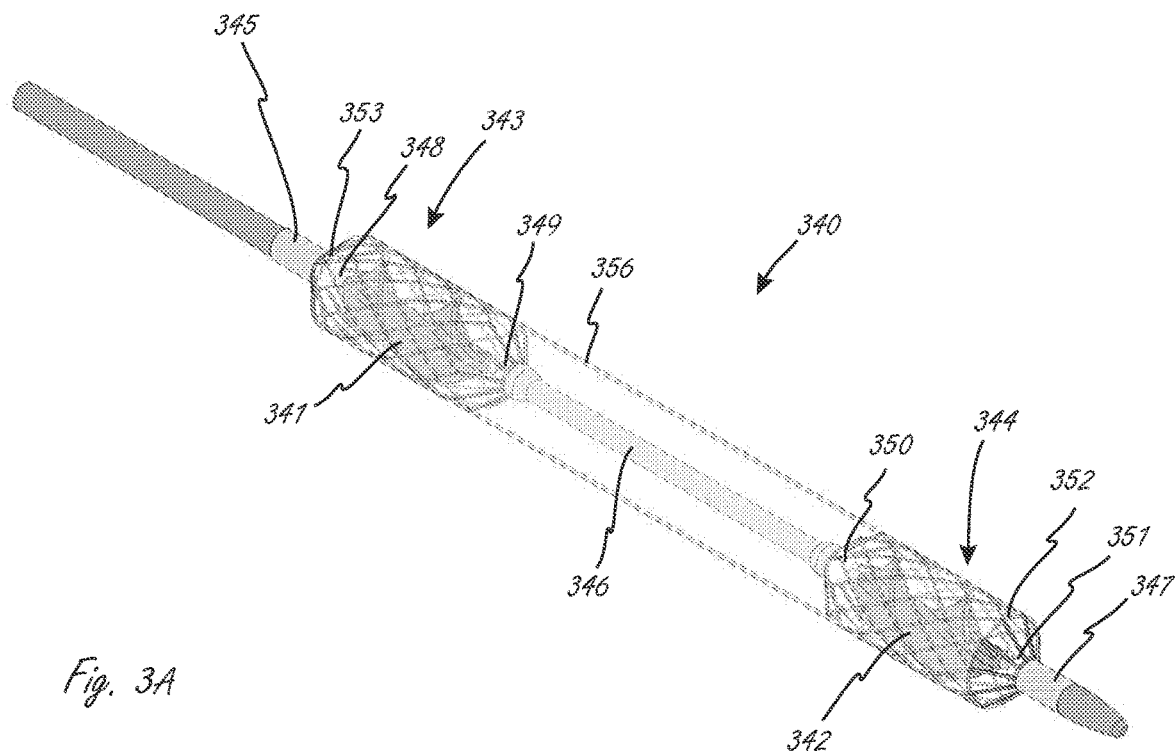
FIGS. 3A, 3B, 3C and 3D illustrate an exemplary expandable pump portion that includes a blood conduit, a plurality of impellers, and a plurality of expandable scaffold sections or support members.
Figure 3B:
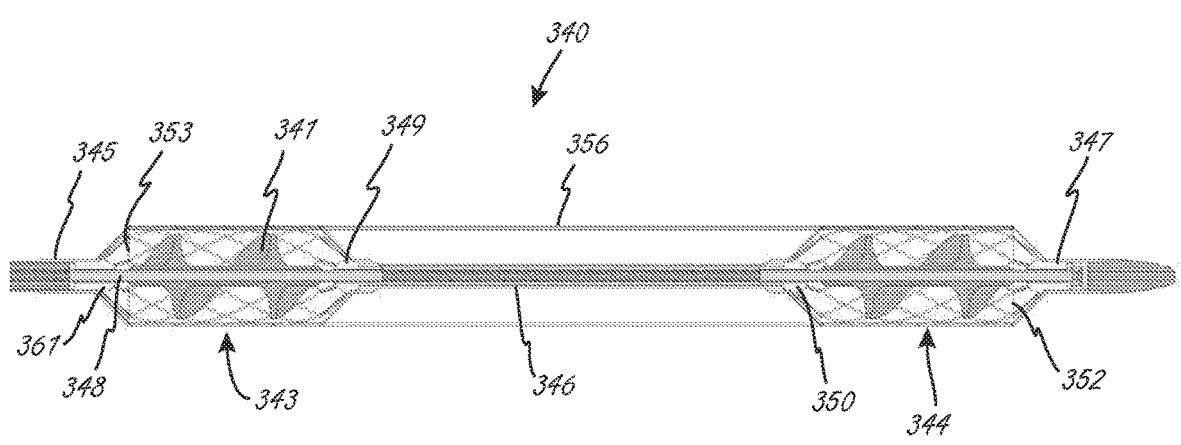
Figure 3C:
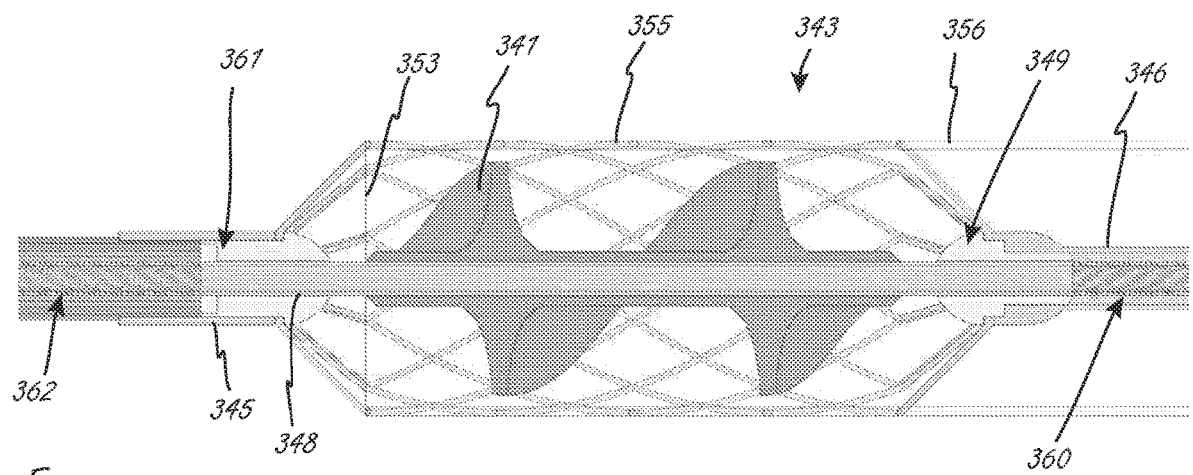
Figure 3D:
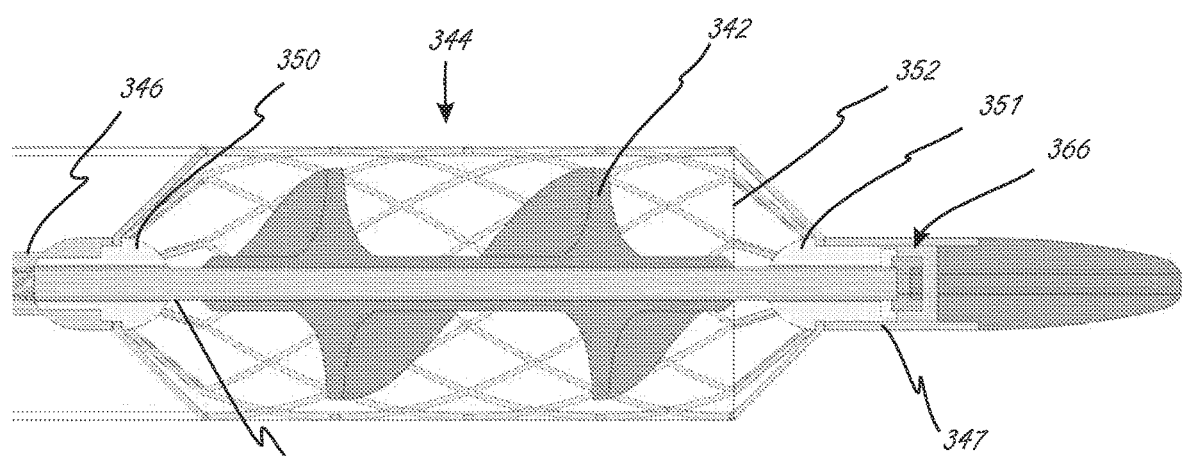

FIGS. 3A-3D show an exemplary pump portion that is similar in some ways to the pump portion shown in FIG. 2. Pump portion 340 is similar to pump portion 1104 in that in includes two expandable members axially spaced from one another when the pump portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Pump portion 340 includes proximal impeller 341 and distal impeller 342, which are coupled to and in operational communication with a drive cable, which defines therein a lumen. The lumen can be sized to accommodate a guidewire, which can be used for delivery of the working portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the working portion, allowing the working portion to be, for example, advanced over a guidewire for positioning the working portion. In this embodiment the second and fourth sections can be stiffer than first and third sections. For example, second and fourth can be tubular and first and third sections can be wound material to impart less stiffness.

Pump portion 340 includes proximal expandable scaffold 343 and distal expandable scaffold 344, each of which extends radially outside of one of the impellers. The expandable scaffolds have distal and proximal ends that also extend axially beyond distal and proximal ends of the impellers, which can be seen in FIGS. 3B-3D. Coupled to the two expandable scaffolds is blood conduit 356, which has a proximal end 353 and a distal end 352. The two expandable scaffolds each include a plurality of proximal struts and a plurality of distal struts. The proximal struts in proximal expandable scaffold 343 extend to and are secured to shaft section 345, which is coupled to bearing 361, through which the drive cable extends and is configured and sized to rotate. The distal struts of proximal expandable scaffold 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts extend axially from distal expandable scaffold 344 to and are secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts extend from the distal expandable scaffold extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
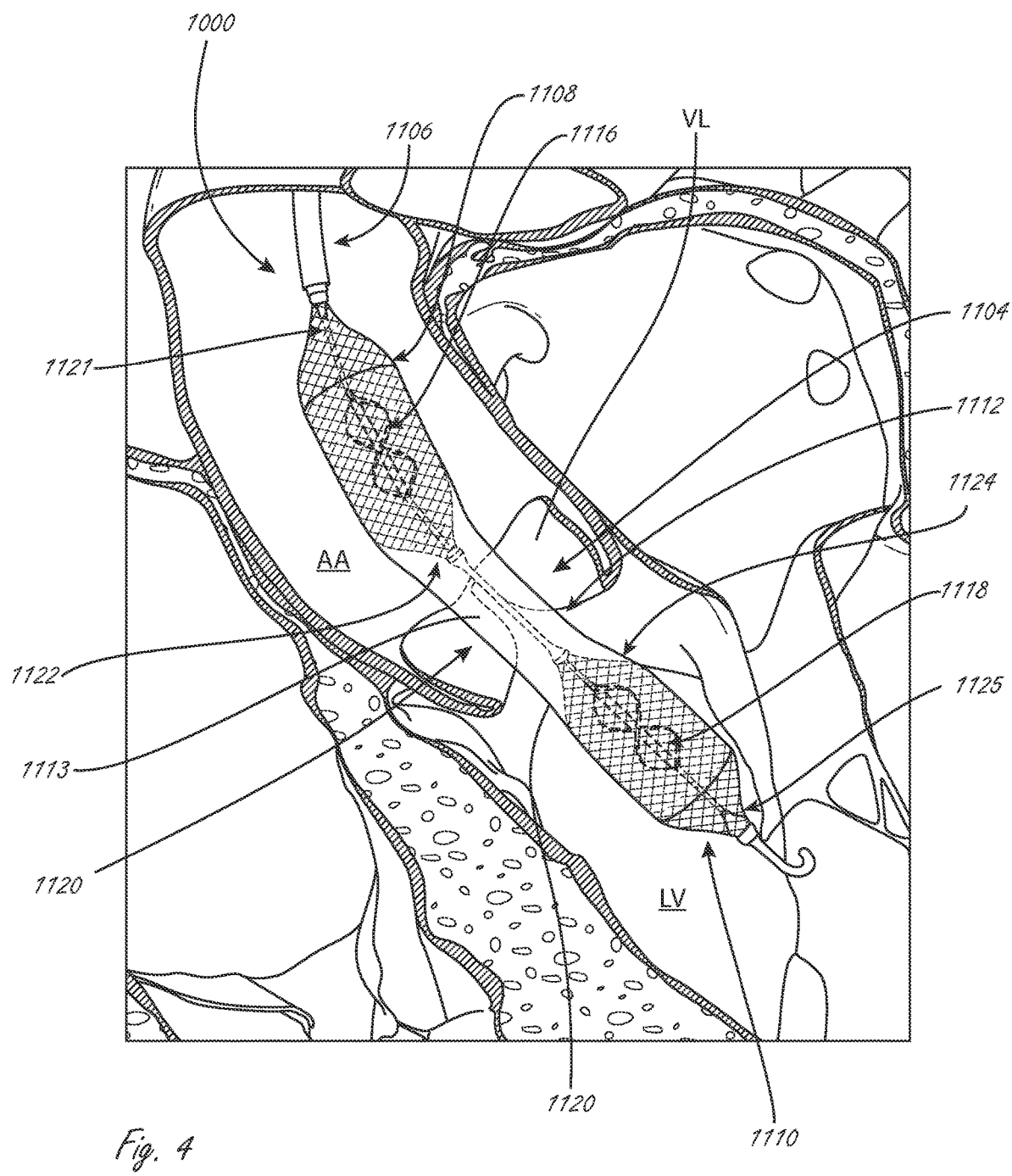
FIG. 4 illustrates an exemplary target location of an expandable pump portion, the pump portion including a blood conduit, a plurality of expandable scaffold sections or support members, and a plurality of impellers.

FIG. 4 illustrates an exemplary placement of pump portion 1104 from catheter blood pump 1000 from FIG. 2. Once difference shown in FIG. 4 is that the conduit extends at least as far as the ends of the impellers, like in FIGS. 3A-3D. FIG. 4 shows pump portion 1104 in a deployed configuration, positioned in place across an aortic valve. Pump portion 1104 can be delivered as shown via, for example without limitation, femoral artery access (a known access procedure). While not shown for clarity, system 1000 can also include an outer sheath or shaft in which working portion 1104 is disposed during delivery to a location near an aortic valve. The sheath or shaft can be moved proximally (towards the ascending aorta "AA" and away from left ventricle "LV") to allow for deployment and expansion of working portion 1104. For example, the sheath can be withdrawn to allow for expansion of second expandable scaffold 1110, with continued proximal movement allowing first expandable scaffold 1108 to expand.

In this embodiment, second expandable scaffold 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable scaffolds 1108 and 1110 causes blood conduit 1112 to assume a more open configuration, as shown in FIG. 4. Thus, while in this embodiment conduit 1112 does not have the same self-expanding properties as the expandable scaffolds, the conduit will assume a deployed, more open configuration when the working end is deployed. At least a portion of central region 1113 of conduit 1112 is positioned at an aortic valve coaptation region and engages leaflets. In FIGS. 3, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable scaffold 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of pump portion 1104, the position of the pump portion can be assessed in any way, such as under fluoroscopy. The position of the pump portion can be adjusted at any time during or after deployment. For example, after second expandable scaffold 1110 is released but before first expandable member 1108 is released, pump portion 1104 can be moved axially (distally or proximally) to reposition the pump portion. Additionally, for example, the pump portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or U.S. Pat. No. 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the working portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the expandable baskets, which can allow for more deformation of the working portion at the location of the leaflets than would occur if an expandable member spanned the aortic valve leaflets. This can cause less damage to the leaflets after the working portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9F sheath and still obtain high enough flow rates when in use, which is not possible with some products currently in development and/or testing. For example, some products are too large to be able to be reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

The embodiment herein can thus achieve a smaller delivery profile while maintaining sufficiently high flow rates, while creating a more deformable and flexible central region of the working portion, the exemplary benefits of which are described above (e.g., interfacing with delicate valve leaflets).

Figure 5:
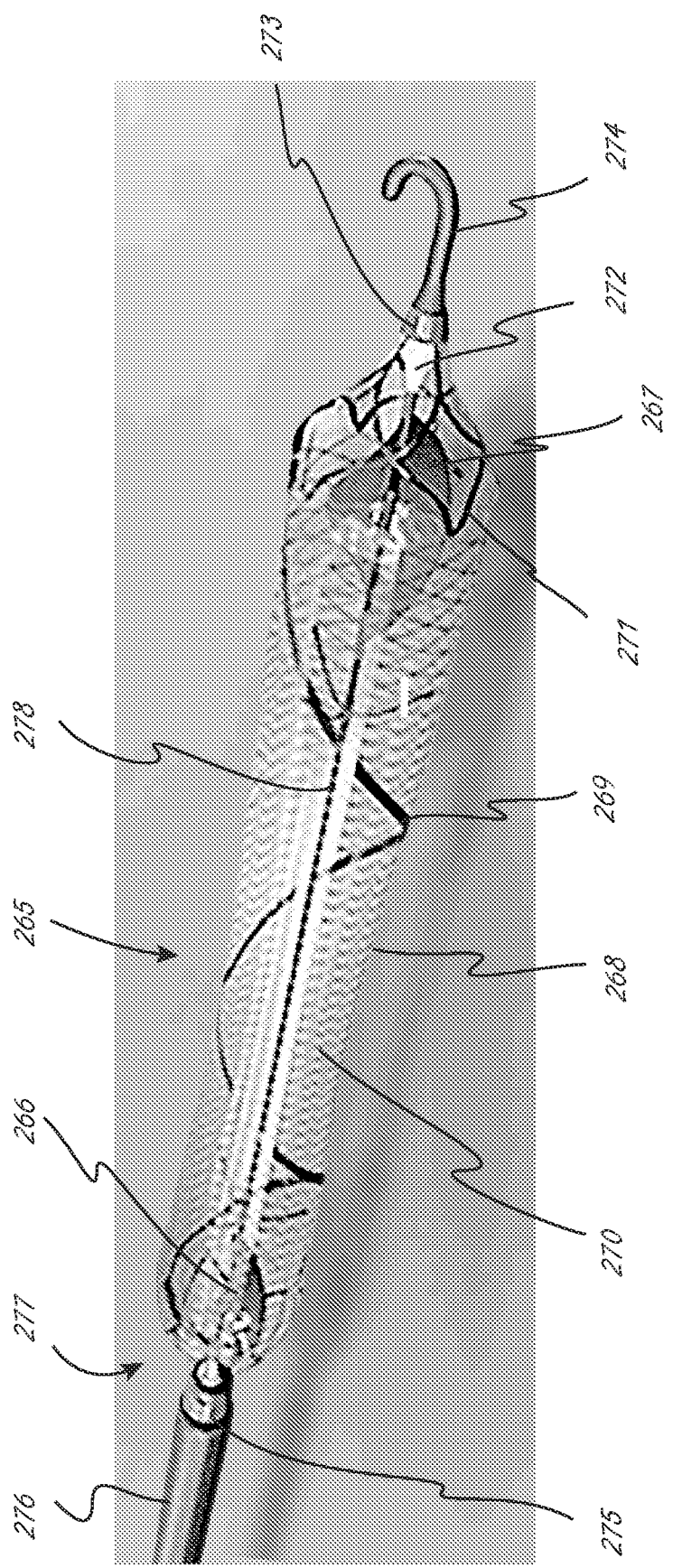
FIG. 5 illustrates an exemplary pump portion including an expandable impeller housing, a blood conduit, and a plurality of impellers.

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable scaffold or member, referred to 270 generally, and blood conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member. Helical tension member 269 (or a helical arrangement of expandable member cells) will act as a collective tension member and is configured so that when the expandable basket is pulled in tension along its length to collapse (such as by stretching to a much greater length, such as approximately doubling in length) tension member 269 is pulled into a straighter alignment, which causes rotation/twisting of the desired segment(s) of the expandable member during collapse, which causes the impeller blades to wrap radially inward as the expandable member and blades collapse. An exemplary configuration of such a tension member would have a curvilinear configuration when in helical form that is approximately equal to the maximum length of the expandable member when collapsed. In alternative embodiments, only the portion(s) of the expandable member that encloses a collapsible impeller is caused to rotate upon collapse.

There are alternative ways to construct the working portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the blood conduits herein act to, are configured to, and are made of material(s) that create a fluid lumen therein between a first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "O." Any of the conduits herein can be impermeable. Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit may extend radially within the expandable member so that inner surface of the conduit is radially within the expandable member where it is secured to the expandable member.

Any of the expandable scaffolds or member(s) herein may be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable scaffold or member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

Figure 6A:
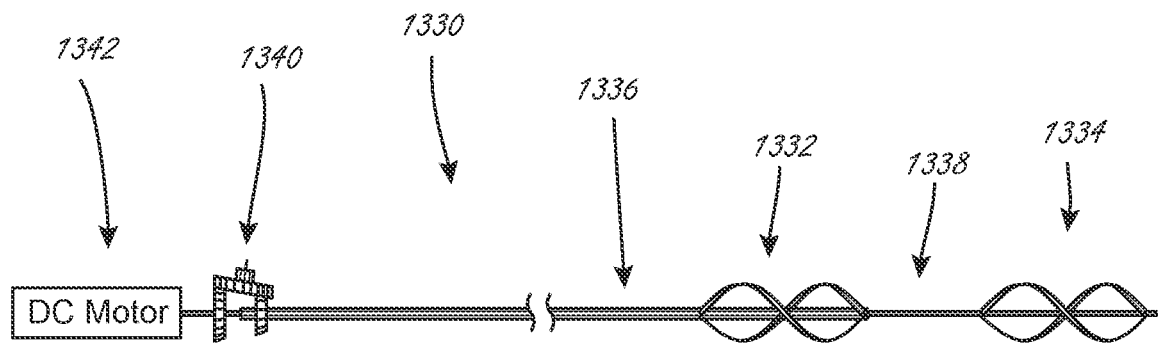
FIG. 6A illustrates at least a portion of an exemplary catheter blood pump that includes a pump portion, wherein at least two different impellers can be rotated at different speeds.

In any of the embodiments herein in which the catheter blood pump includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

Figure 6B:
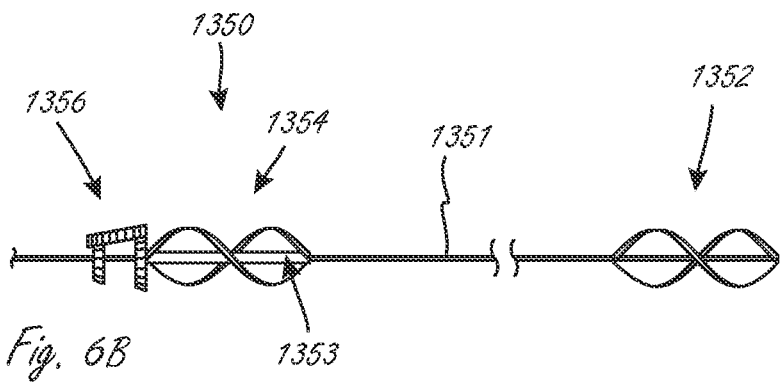
FIG. 6B illustrates at least a portion of an exemplary catheter blood pump that includes a pump portion, where at least two different impellers can be rotated at different speeds.

FIG. 6B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 6A. FIGS. 6A and 6B illustrate how a gearset can be adapted to drive the proximal impeller slower or faster than the distal impeller.

Figure 7:
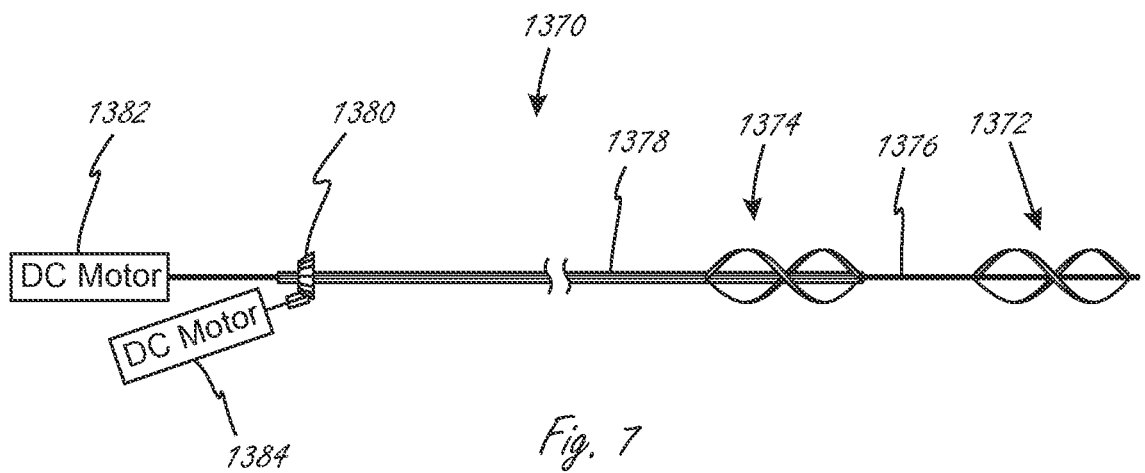
FIG. 7 illustrates a portion of an exemplary catheter blood pump that includes a pump portion.

FIG. 7 illustrates an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

Figure 6C:
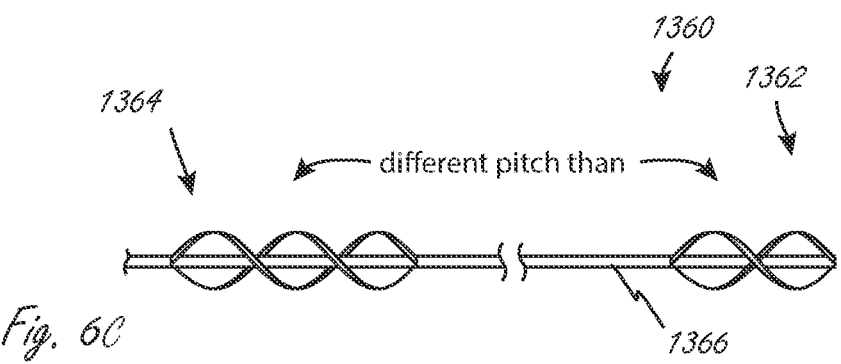
FIG. 6C illustrates at least a portion of an exemplary catheter blood pump that includes a pump portion with at least two impellers having different pitches.

In some embodiments, a common drive mechanism (e.g., cable and/or shaft) can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 6C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions (or distal portions) herein with a plurality of impellers can be modified to include first and second impellers with different pitches.

In any of the embodiments herein, the pump portion may have a compliant or semi-compliant (referred to generally together as "compliant") exterior structure. In various embodiments, the compliant portion is pliable. In various embodiments, the compliant portion deforms only partially under pressure. For example, the central portion of the pump may be formed of a compliant exterior structure such that it deforms in response to forces of the valve. In this manner the exterior forces of the pump on the valve leaflets are reduced. This can help prevent damage to the valve at the location where it spans the valve.

Figure 8:
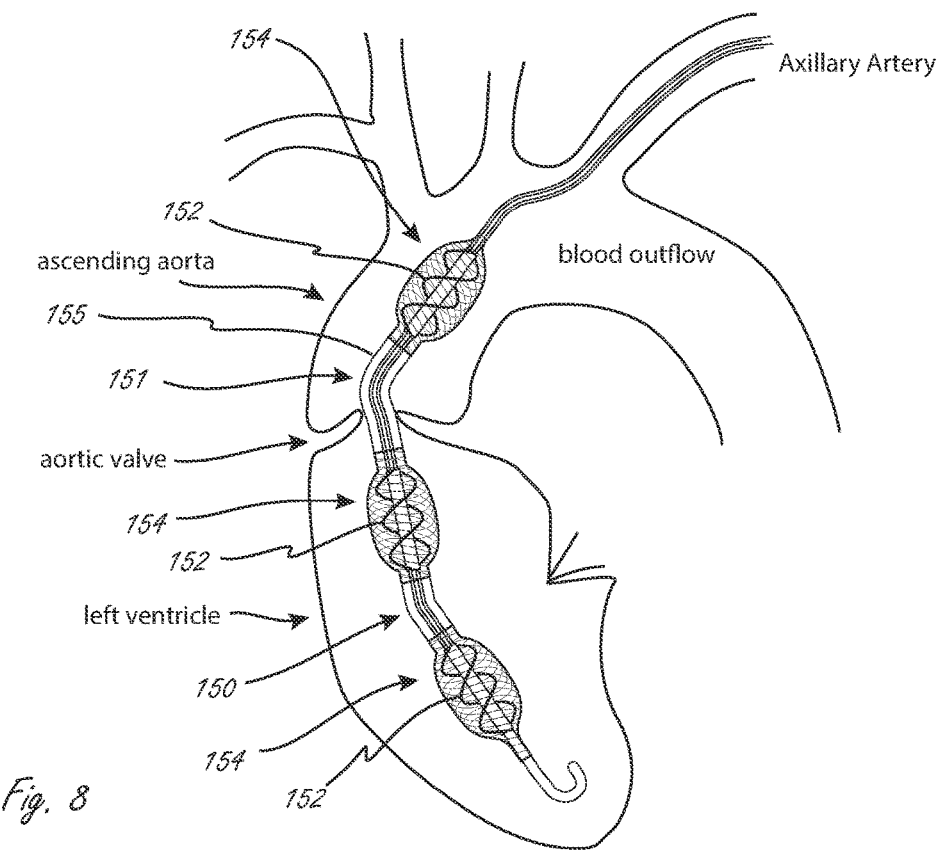
FIG. 8 illustrates an exemplary expandable pump portion including a plurality of expandable impellers, including one or more bends formed therein between adjacent impellers.

FIG. 8 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1. In FIG. 8, a fluid lumen extends from a distal end to a proximal end, features of which are described elsewhere herein. The embodiment in FIG. 8 can include any other suitable feature, including methods of use, described herein.

The embodiment in FIG. 8 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 8. In this method of placement, a central impeller and distal-most impeller are positioned in the left ventricle, and a proximal-most impeller is positioned in the ascending aorta. Bend 151 is positioned just downstream to the aortic valve.

A bend such as bend 150 or 151 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 8, the pump is positioned via the axillary artery, which is an exemplary method of accessing the aortic valve, and which allows the patient to walk and be active with less interruption. Any of the devices herein can be positioned via the axillary artery. It will be appreciated from the description herein, however, that the pump may be introduced and tracked into position in various manners including a femoral approach over the aortic arch.

One aspect of the disclosure is a catheter blood pump that includes a distal impeller axially spaced from a proximal impeller. Distal and proximal impellers may be axially spaced from each other. For example, the distal and proximal impellers may be connected solely by their individual attachment to a common drive mechanism. This is different from a single impeller having multiple blade rows or sections. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse. The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. It can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

Figure 9:
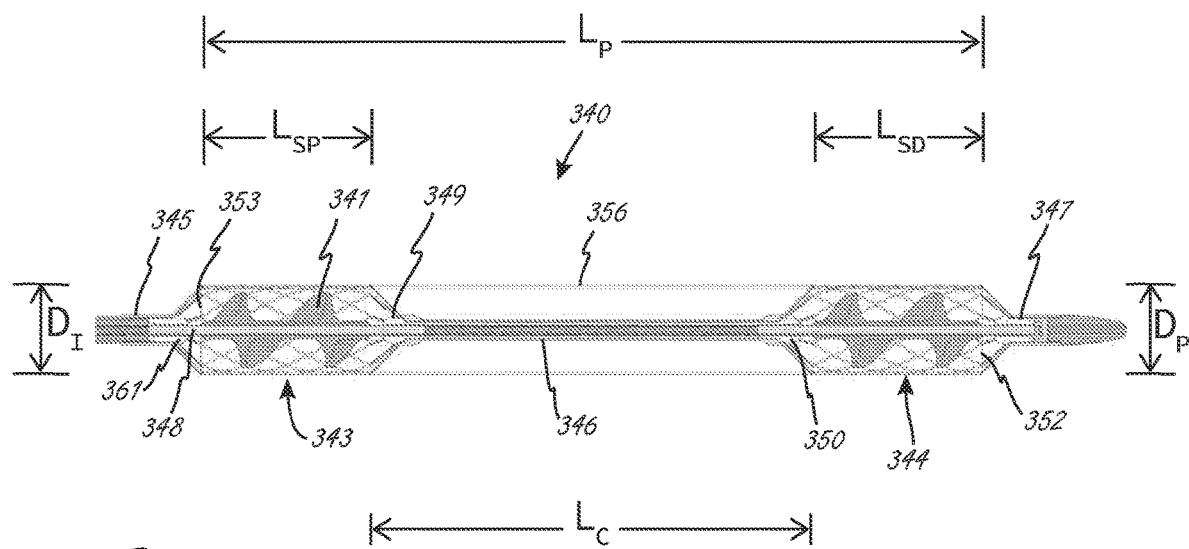
FIG. 9 illustrates an exemplary expandable pump portion comprising a plurality of impellers and a blood conduit.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 9 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between the impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 9), from 0.5 cm to 10 cm, or any subrange thereof. The examples below provide exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 cm to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 9. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the housing can have a deployed diameter, at least the location of an impeller (and optionally at a location between impellers), shown as dimension Dp in FIG. 9. In some embodiments Dp can be from 0.3 cm to 1.5 cm, or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension Di in FIG. 9. In some embodiments Di can be from 1 mm-30 mm, or any subrange therein. For example, in some embodiments Di may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm -1 mm, such as 0.05 mm to 0.8 mm, or such as 0.1 mm-0.5 mm.

In any of the embodiments herein that includes multiple impellers, the axial spacing between impellers (along the length of the pump portion, even if there is a bend in the pump portion) can be from 2 mm to 100 mm, or any combination of upper and lower limits inclusive of 5 and 100 mm (e.g., from 10 mm-80 mm, from 15 mm-70 mm, from 20 mm-50 mm, 2 mm-45 mm, etc.).

Any of the pump portions herein that include a plurality of impellers may also include more than two impellers, such as three, four, or five impellers (for example).

Figure 10:
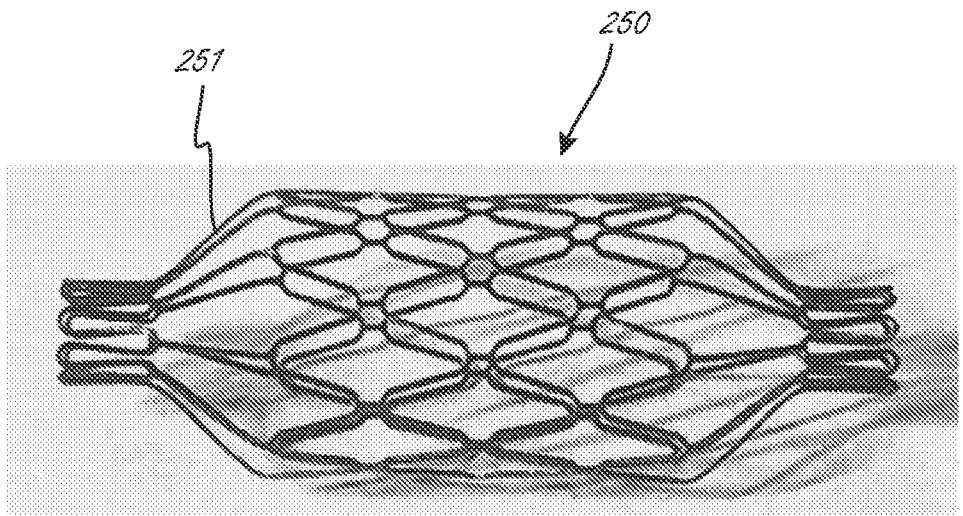
FIG. 10 illustrates an exemplary scaffold design and exemplary struts.

FIG. 10 illustrates an expandable scaffold 250 that may be one of at least two expandable scaffolds of a pump portion, such as the expandable scaffolds in FIGS. 3A-3D, wherein each expandable scaffold at least partially surrounds an impeller. The scaffold design in FIG. 10 has proximal struts 251 (only one labeled) extending axially therefrom. Having a separate expandable scaffold 250 for each impeller provides for the ability to have different geometries for any of the individual impellers. Additionally, this design reduces the amount of scaffold material (e.g., Nitinol) over the length of the expandable blood conduit, which may offer increased tracking when sheathed. A potential challenge with these designs may include creating a continuous membrane between the expandable scaffolds in the absence of an axially extending scaffolding material (see FIG. 3A). Any other aspect of the expandable scaffolds or members herein, such as those described in FIGS. 3A-3D, may be incorporated by reference into this exemplary design. Struts 251 may be disposed at a pump inflow or outflow. Struts 251 may be proximal struts or they may be distal struts.

Figure 11:
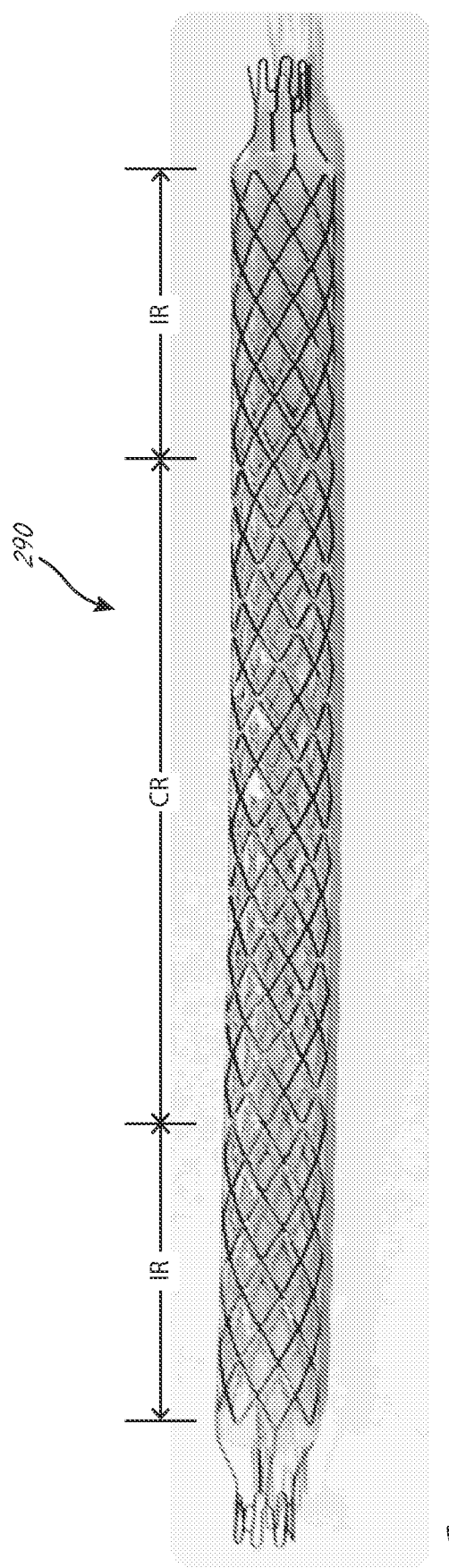
FIG. 11 illustrate an exemplary scaffold design and exemplary struts.

FIG. 11 show an exemplary scaffold along an length of the blood conduit. Central region "CR" may be axially between proximal and distal impellers. Central region "CR" flexibility is increased relative to scaffold impeller regions "IR" due to breaks or discontinuities in the scaffold pattern in the central region. The scaffold has relatively more rigid impeller sections "IR" adjacent the central region where impellers may be disposed (not shown). The relatively increased rigidity in the impeller regions IR may help maintain tip gap and impeller concentricity. This pump scaffold pattern provides for a flexibility distribution, along its length, of a proximal section of relatively less flexibility ("IR"), a central region "CR" of relatively higher flexibility, and a distal section "IR" of relatively less flexibility than the central region. The relatively less flexible sections (i.e., the two IR regions) are where proximal and distal impellers may be disposed (not shown but other embodiments are fully incorporated herein in this regard), with a relatively more flexible region in between. Exemplary benefits of the relative flexibility in these respective sections are described elsewhere herein. FIG. 11 is an example of a scaffold that is continuous from a first end region to a second end region, even though there are breaks or discontinuities in some locations of the scaffold. There is at least one line that can be traced along a continuous structural path from a first end region to a second end region.

The following disclosure provides exemplary method steps that may be performed when using any of the blood pumps, or portions thereof, described herein. It is understood that not all of the steps need to be performed, but rather the steps are intended to be an illustrative procedure. It is also intended that, if suitable, in some instances the order of one or more steps may be different. Before use, the blood pump can be prepared for use by priming the lumens (including any annular spaces) and pump assembly with sterile solution (e.g., heparinized saline) to remove any air bubbles from any fluid lines. The catheter, including any number of purge lines, may then be connected to a console. Alternatively, the catheter may be connected to a console and/or a separate pump that are used to prime the catheter to remove air bubbles.

Figure 12A:
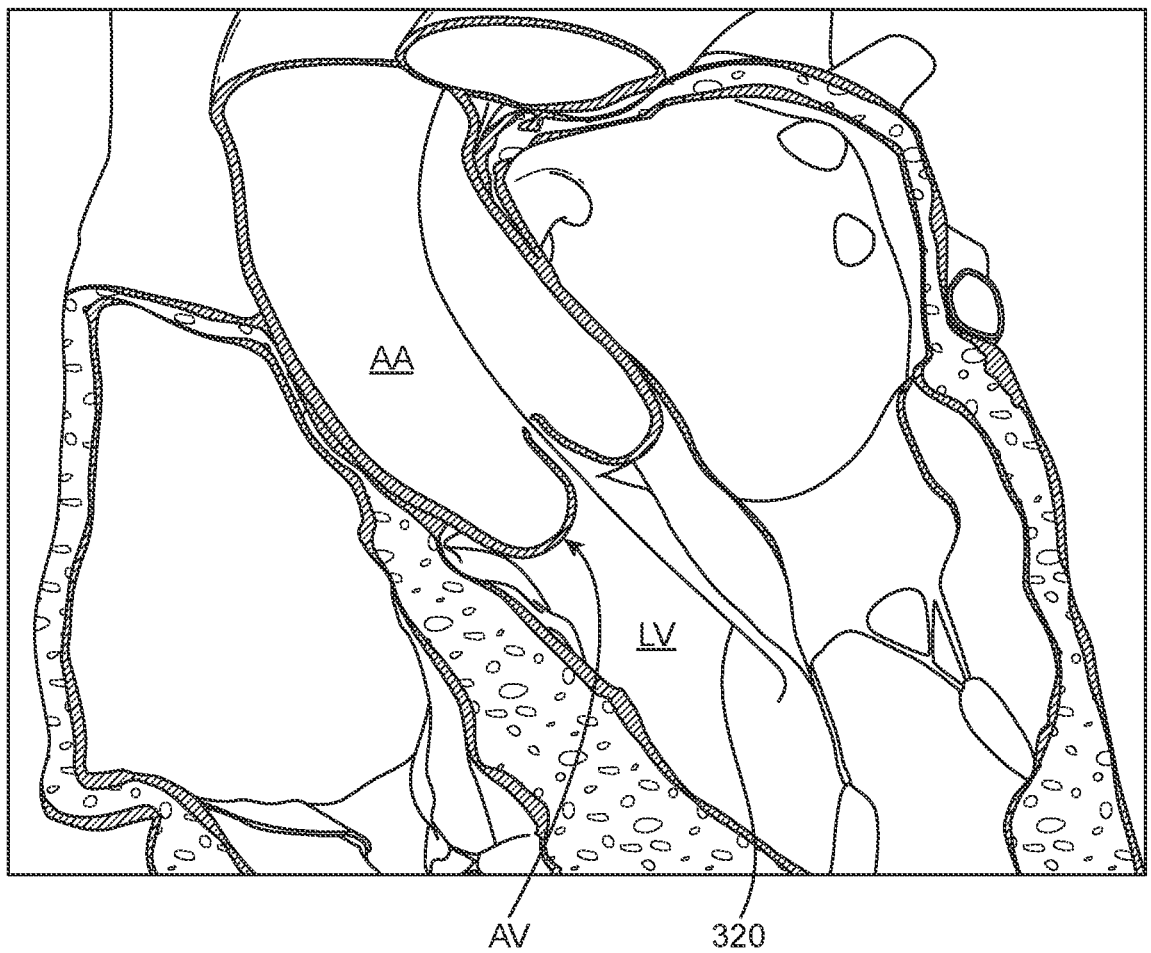
FIGS. 12A-12F illustrate an exemplary sequence of steps that may be performed to deploy an exemplary pump portion of a catheter blood pump.
Figure 12B:
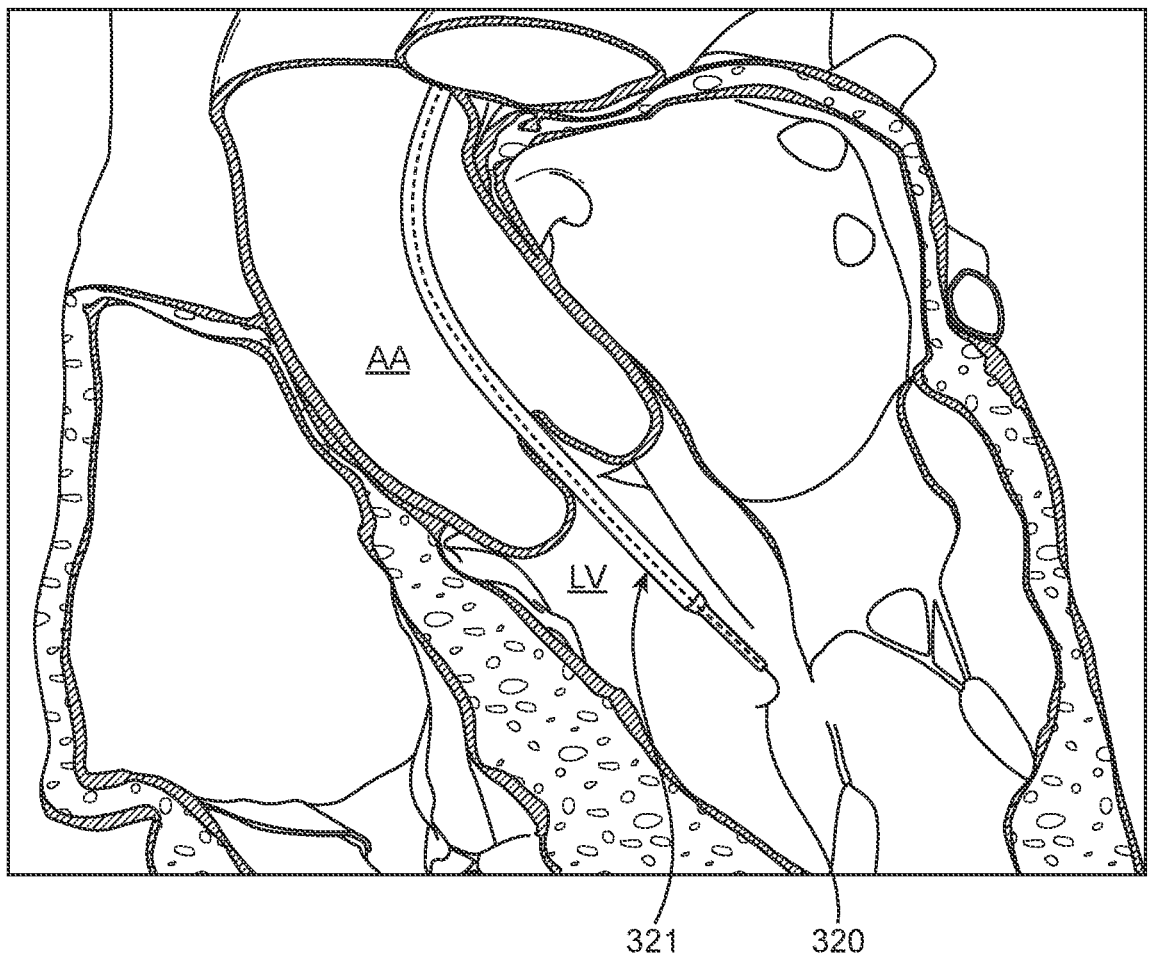

After priming the catheter, access to the patient's vasculature can be obtained (e.g., without limitation, via femoral access) using an appropriately sized introducer sheath. Using standard valve crossing techniques, a diagnostic pigtail catheter may then be advanced over a, for example, 0.035" guide wire until the pigtail catheter is positioned securely in the target location (e.g., left ventricle). The guidewire can then be removed and a second wire 320 (e.g., a 0.018" wire) can be inserted through the pigtail catheter. The pigtail catheter can then be removed (see FIG. 12A), and the blood pump 321 (including a catheter, catheter sheath, and pump portion within the sheath; see FIG. 12B) can be advanced over the second wire towards a target location, such as spanning a aortic valve "AV," and into a target location (e.g., left ventricle "LV"), using, for example, one or more radiopaque markers to position the blood pump.

Figure 12C:
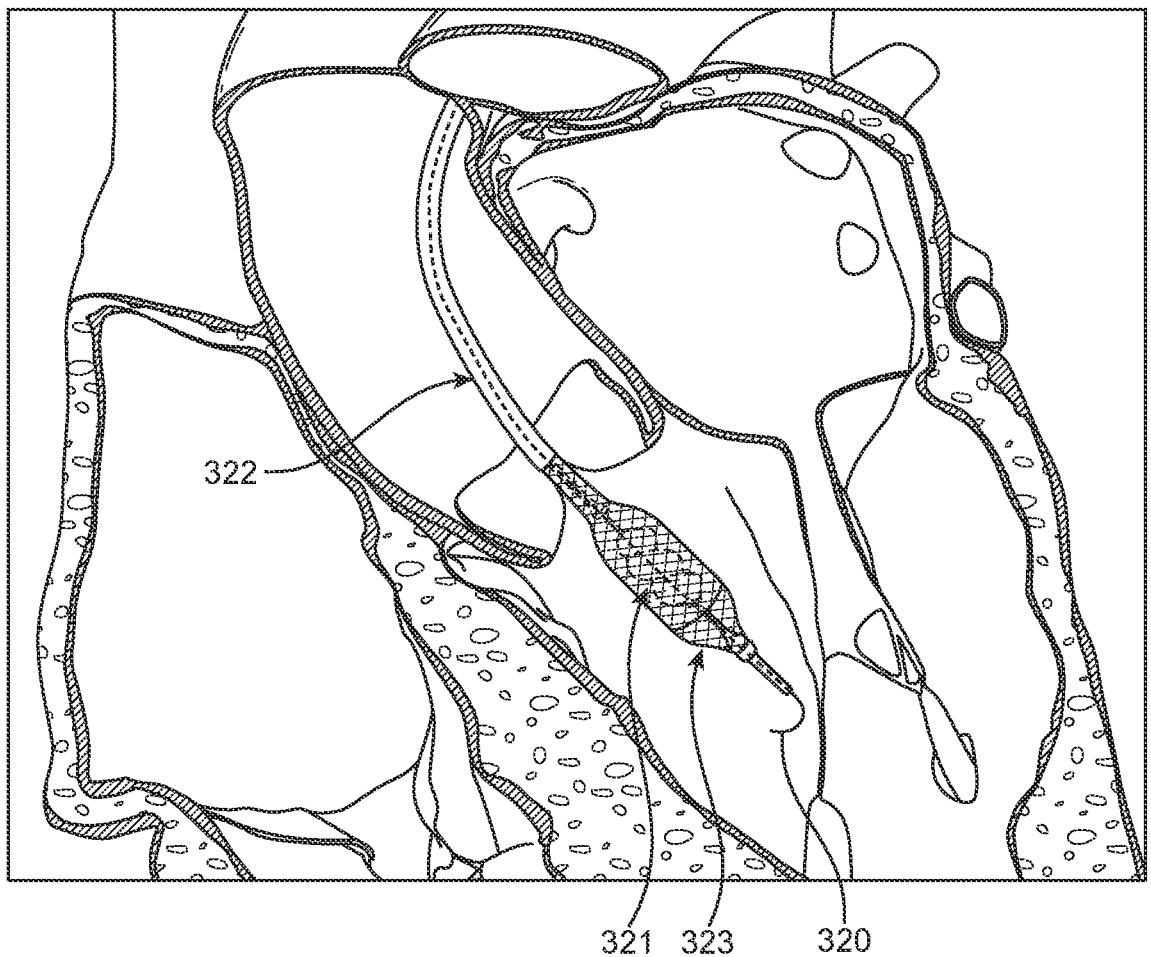
Figure 12D:
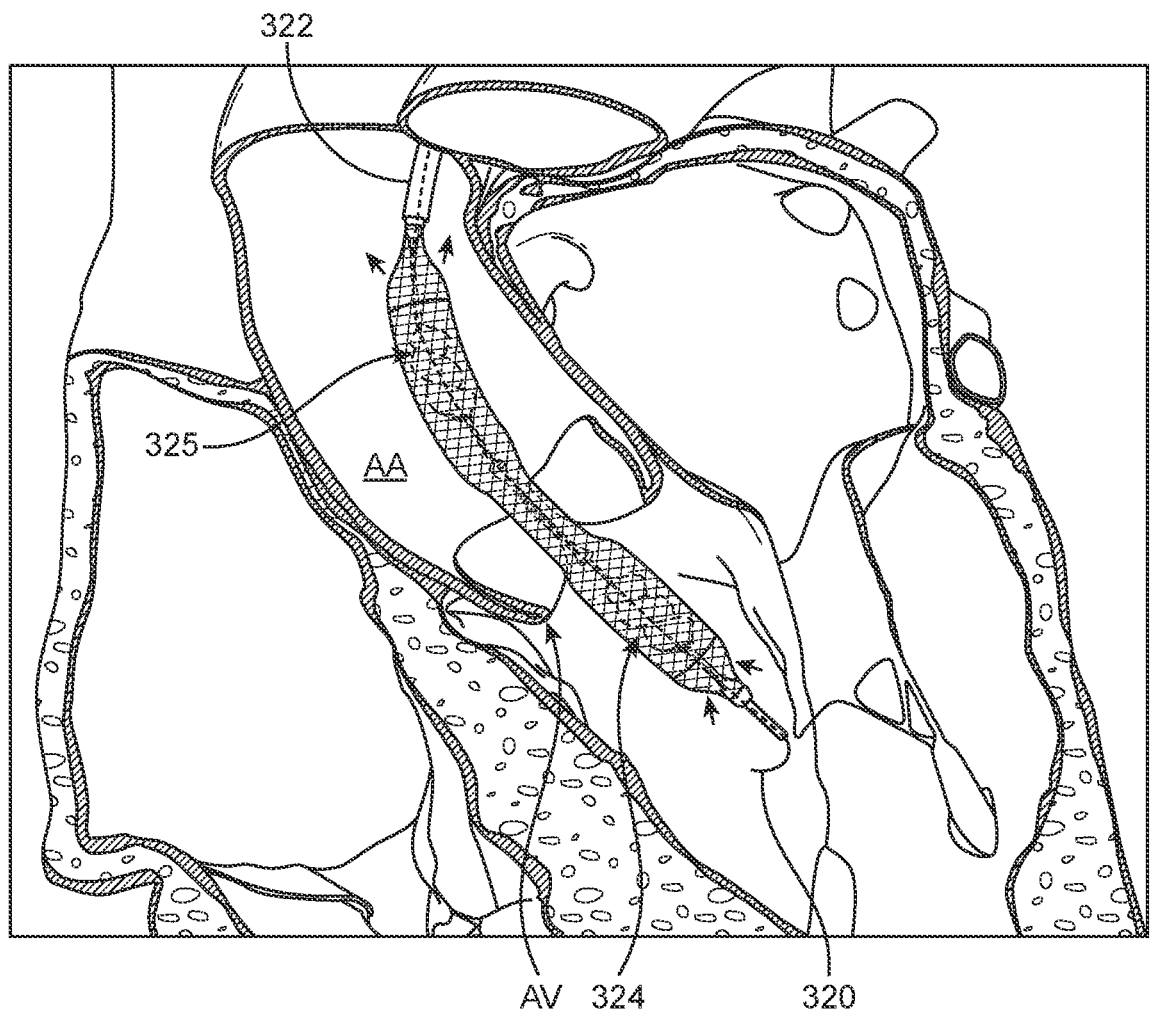

Once proper placement is confirmed, the catheter sheath 322 (see FIG. 12C) can be retracted, exposing first a distal region of the pump portion. In FIG. 12C a distal region of an expandable housing has been released from sheath 322 and is expanded, as is distal impeller 324. A proximal end of housing 323 and a proximal impeller are not yet released from sheath 322. Continued retraction of sheath 322 beyond the proximal end of housing 323 allows the housing 323 and proximal impeller 325 to expand (see FIG. 12D). The inflow region (shown with arrows even though the impellers are not yet rotating) and the distal impeller are in the left ventricle. The outflow (shown with arrows even though the impellers are not rotating yet) and proximal impeller are in the ascending aorta AA. The region of the outer housing in between the two impellers, which may be more flexible than the housing regions surrounding the impellers, as described in more detail herein, spans the aortic valve AV. In an exemplary operating position as shown, an inlet portion of the pump portion will be distal to the aortic valve, in the left ventricle, and an outlet of the pump portion will be proximal to the aortic valve, in the ascending aorta ("AA").

Figure 12E:
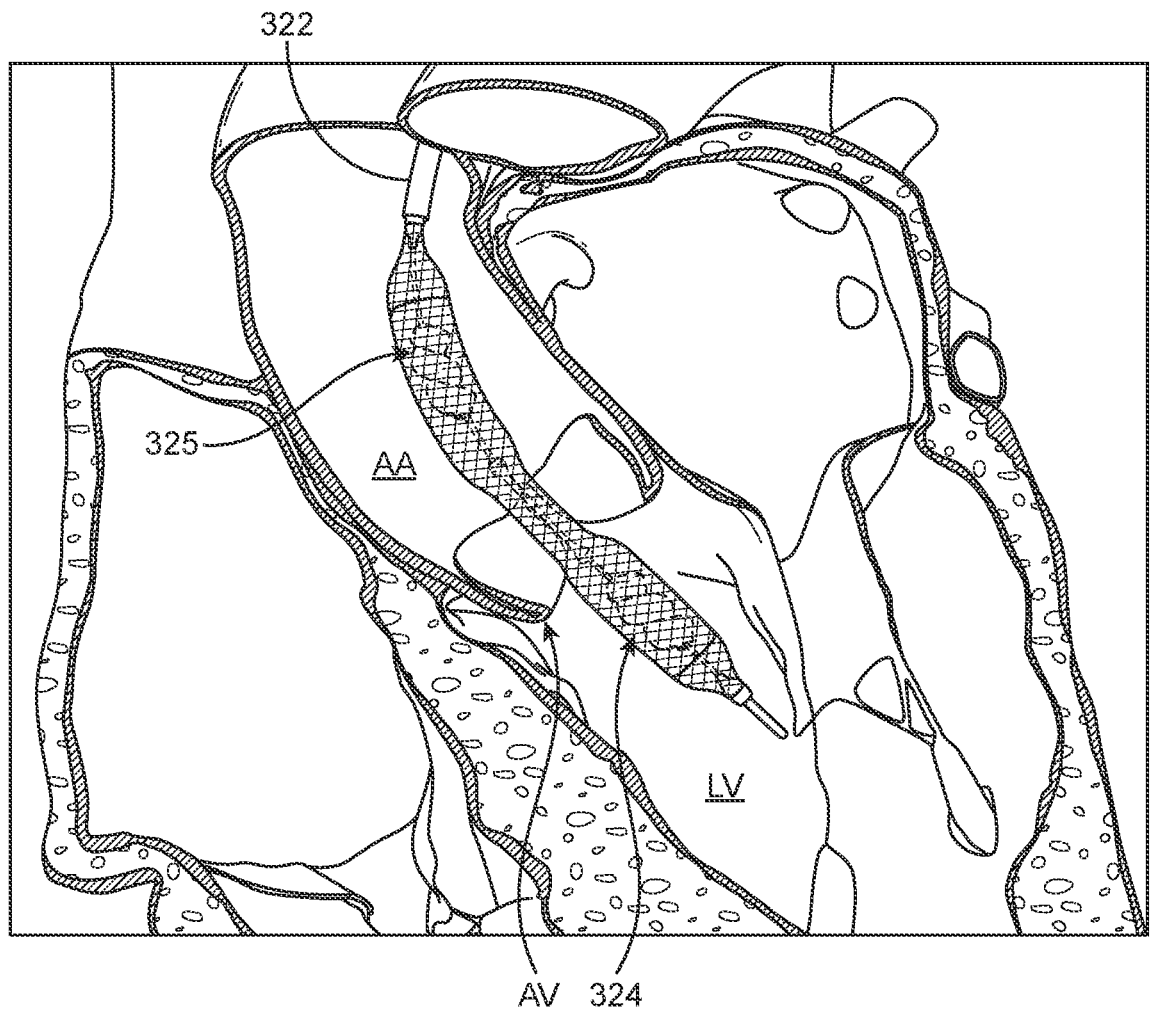
Figure 12F:
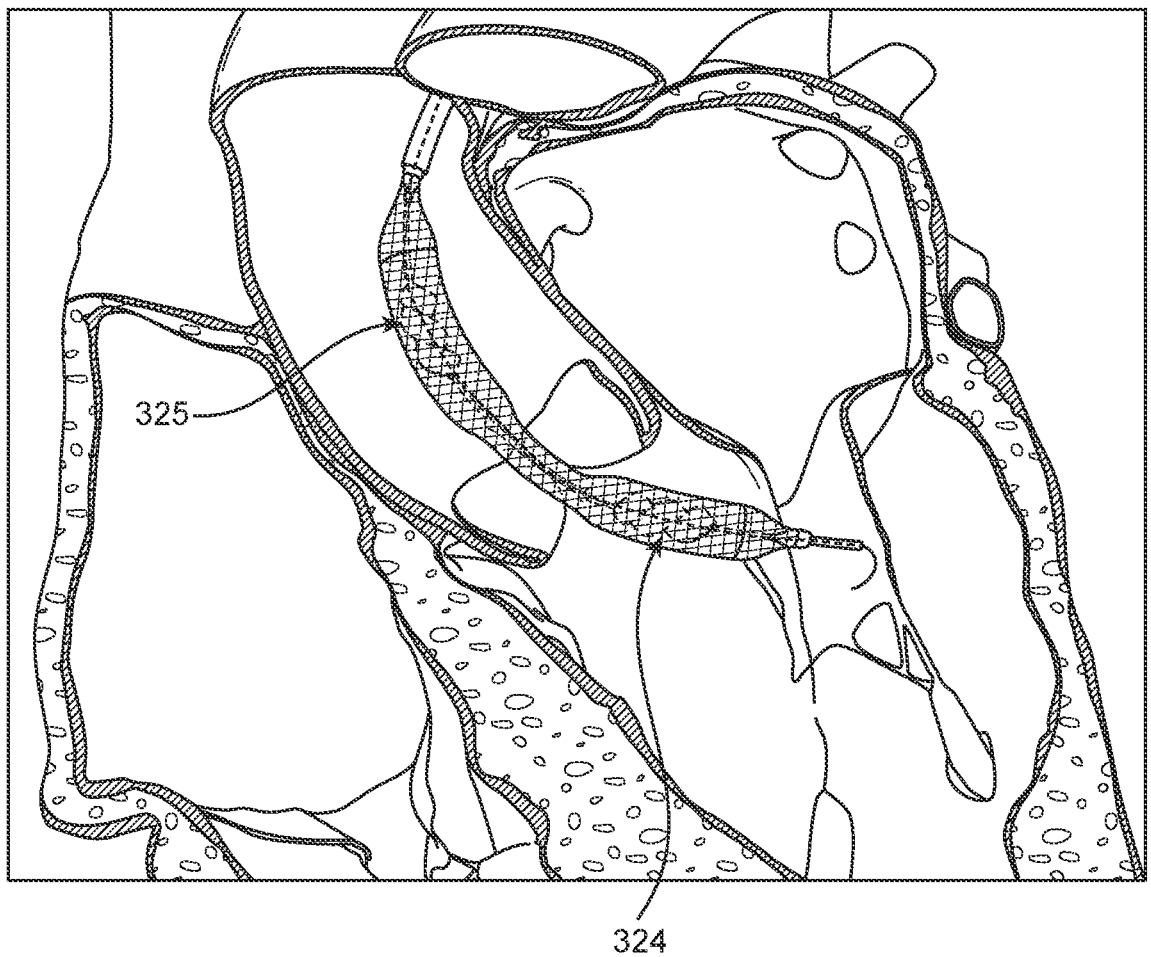

The second wire (e.g., an 0.018" guidewire) may then be moved prior to operation of the pump assembly (see FIG. 12E). If desired or needed, the pump portion can be deflected (active or passively) at one or more locations as described herein, as illustrated in FIG. 12F. For example, a region between two impellers can be deflected by tensioning a tensioning member that extends to a location between two impellers. The deflection may be desired or needed to accommodate the specific anatomy. As needed, the pump portion can be repositioned to achieve the intended placement, such as, for example, having a first impeller on one side of a heart valve and a second impeller on a second side of the heart valve. It is understood that in FIG. 12F, the pump portion is not in any way interfering or interacting with the mitral valve, even if it may appear that way from the figure.

Some pump portions herein may include one or more expandable struts, the struts extending axially from an end region of the expandable blood conduit, such as in FIGS. 3A-3D, 5, 9, 10 and 11 for example. The struts may be disposed at an outflow of the pump portion or an inflow of the pump portion. For example, distal struts 271 shown in FIG. 5 are disposed in or at an inflow of the exemplary pump portion. Additionally, for example, proximal struts 251 shown in FIG. 10 may be disposed in or at an inflow or an outflow of a pump portion. The struts herein are coupled or secured to the expandable blood conduit, and couple the expandable blood conduit to sections of the catheter pump that are distal and proximal to the expandable blood conduit, and are adapted and configured for expansion and collapse to allow the expandable blood conduit to expand and collapse.

In some embodiments herein, struts that extend axially from an end region of the expandable blood conduit may not be unitary with the expandable blood conduit. In these embodiments, the struts are not formed from the same starting material as a portion of the expandable blood conduit, but rather are components that are secured or coupled (e.g., directly attached) to one or more components of the expandable blood conduit. For example, some expandable blood conduits herein include an expandable scaffold, which may also be referred to herein as an expandable support member, and which provides radial support to the blood conduit when expanded. In some embodiments a plurality of struts that extend from an end region of the blood conduit are non-unitary with an expandable scaffold at the end region. First and second components herein that are described as being non-unitary are components that are not formed from the same starting material, and are coupled or secured together at some time. In some instances herein, components that are described as being integrally formed may refer to materials that are made from the same starting material. This disclosure also includes pump portions of catheter blood pumps that include one or more expandable scaffolds that are not unitary with one or more struts extending from an end region of the expandable scaffold.

Pump portions that include expandable blood conduits (which may include a radially supporting scaffold) that are non-unitary with a plurality of struts extending axially therefrom may provide one or more advantages. For example, one or more aspects of manufacturing the scaffold may be easier if a plurality of struts extending therefrom are not included in one or more assembly steps. For example, methods of manufacturing may include coupling one or more scaffolds to polymeric materials (e.g., membranes) that may define at least part of a blood conduit herein. This type of process may be performed on a mandrel. In some instances, for example, there may be advantages to coupling one or more scaffolds to a membrane (e.g., on a mandrel) without having struts extending from a scaffold when securing the scaffold(s) to the membrane(s). A method of manufacturing may include first creating a sub-assembly of scaffold and membrane, and at a subsequent time attaching a plurality of struts to the sub-assembly. In these exemplary methods of manufacture, one or more layers of a polymeric material may be deposited on a mandrel, and one or more scaffold sections may be applied over (e.g., on) that the one or more polymeric layers. Optionally, one or more additional polymeric layers may be applied over (e.g., on) the one or more scaffold sections, sandwiching the one or more scaffold sections within inner and outer layers. Inner and outer layers in this context may each comprise one or more layers of material (e.g., polymeric material).

At a time subsequent to assembling the expandable blood conduit, one or more non-unitary struts may be coupled to (e.g., directly attached to) one or more end regions of the expandable blood conduit, such as one or both of a proximal end region or a distal end region of the blood conduit. In general, if non-unitary struts are secured to first and second end regions of a blood conduit, struts in a first group of struts that are secured to a first end region are generally referred to together as a plurality of struts, and struts in a second group of struts that are secured to a second end region (which is different than the first end region) are generally referred to together as a plurality of struts, where the first plurality of struts is a different plurality than the second plurality of struts.

An additional exemplary advantage of blood pumps that comprise struts that are not unitary with an expandable blood conduit is that different materials or physical characteristics may be imparted to the struts and blood conduit component(s) (e.g. a scaffold), which may provide more design options for struts and blood conduit components. For example without limitation, struts and scaffold sections that are attached may be different materials, they may have different stiffness, different dimension, and/or it may be easier to configure the struts with a particular expanded configuration.

In any embodiment in which the struts are not unitary with a scaffold of a blood conduit, the struts and scaffold (which may also be referred to herein as an expandable support member) may be attached using a wide variety of techniques and concepts. For example only, any suitable mechanical coupling may be used, such as a female-male type of attachment. The attachments may also include any number of optional manufacturing steps, such as applying a force to the coupled components to cause some deformation to one or more components, or using an adhesive or weld to further strengthen the coupling. Strands of material (e.g., thread, filament, wire) may optionally be used to help secure struts to an end region of a scaffold. Once coupled, the struts are adapted to collapse radially inward for delivery, expand for deployment, and collapse again upon removal of the pump portion from the patient. In any of the embodiments herein the struts may be secured to the scaffold, at least partially, by welding or other bonding of the struts and scaffold together. Any of the struts and scaffolds herein may be secured together using any of the one or more coupling concepts and techniques herein, such as without limitation, a mechanical coupling and additionally welded.

Figure 13A:
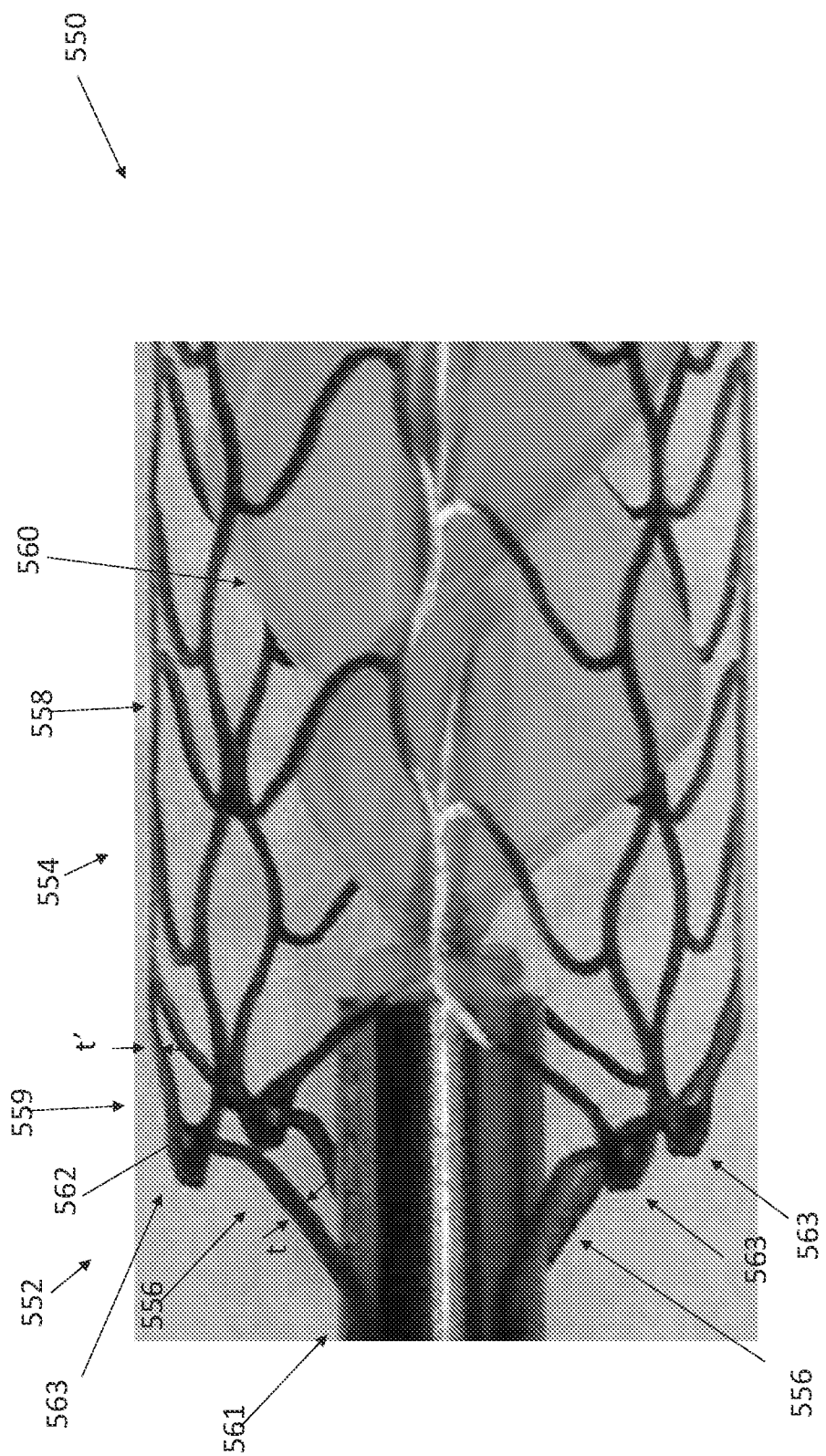
FIG. 13A illustrates exemplary struts that are non-unitary with and coupled to an expandable blood conduit, including an expandable scaffold.
Figure 13B:
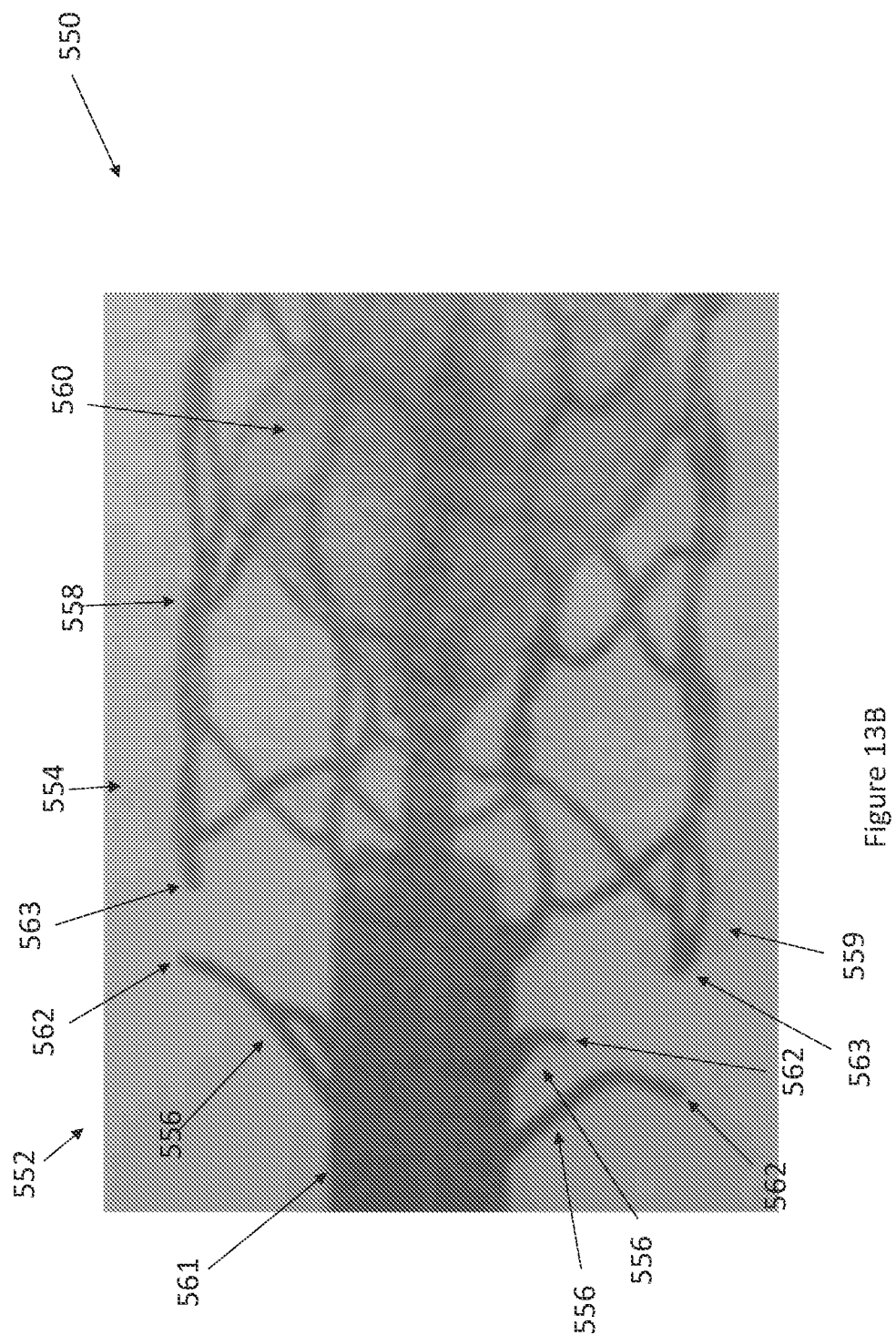
FIG. 13B illustrates exemplary struts that are non-unitary with and not coupled to an expandable blood conduit, including an expandable scaffold.

FIGS. 13A and 13B illustrate a portion of an exemplary pump portion of a catheter pump, and not all components are shown for clarity. The pump portion 550 includes an expandable impeller housing 552 that includes an expandable blood conduit 554 and a plurality of struts 556 (only two of the four struts that are shown are labeled) extending axially from an end region of the expandable blood conduit. In this example the plurality of struts 556 are non-unitary with the expandable blood conduit, and are non-unitary with scaffold 558, but in FIG. 13A are shown coupled and attached directly to scaffold 558 of the blood conduit 554. A membrane (e.g., one or more polymeric layers) is not illustrated in FIGS. 13A and 13B for clarity, but it is understood that the expandable impeller housing in FIGS. 13A and 13B may comprise any of the membranes herein that are coupled to an expandable scaffold. In this example, struts 556 extend between strut hub 561 and scaffold 558. Any of the scaffolds in any particular embodiment herein may have any of the scaffold patterns herein.

The portion of the exemplary pump portion shown in FIGS. 13A and 13B may be a proximal region of an expandable pump portion. In these examples, FIGS. 13A and 13B illustrate a plurality of proximal struts 556 that are non-unitary with a proximal end region 559 of an expandable scaffold. Struts 556 are shown extending axially (proximally in this example) from proximal end region 559. A portion of exemplary impeller 560 is also shown, which includes a plurality of impeller blades as shown. Struts 556 may be at an inflow or an outflow of the expandable impeller housing 552 of the pump portion 550.

The portion of the exemplary pump portion shown in FIGS. 13A and 13B may alternatively be a distal region of an expandable pump portion. In these examples, FIGS. 13A and 13B illustrate a plurality of distal struts 556 that are non-unitary with a distal end region 559 of expandable scaffold (distal is to the left in the figure in this example). Struts 556 are shown extending distally from distal end region 559. A portion of exemplary impeller 560 is also shown, which includes a plurality of impeller blades as shown. Struts 556 may be at an inflow or an outflow of the expandable impeller housing 552. The impeller may be a distal impeller and the pump may optionally also include a proximal impeller, examples of which are described herein. Any other aspect of any catheter blood pump herein or incorporated by reference may be included in these exemplary pump portion, such as any of the motor and/or fluid delivery (e.g., purge, lubricating).

In some examples, both an inflow and an outflow of an expandable impeller housing may include a plurality of struts extending from an end region of a blood conduit and are non-unitary with an expandable scaffold at the end regions. For example, any of the pump portions herein may include an expandable impeller housing that includes a first plurality of struts extending from a proximal end region of a blood conduit that are non-unitary with a scaffold at the proximal end region, and the expandable impeller housing may also include a second plurality of struts extending from a distal end region of a blood conduit that are non-unitary with a scaffold at the distal end region. The scaffolds may be part of the same or common scaffold structure, or they may be separate scaffold sections such as in FIGS. 3A-3D, for example. For example, an expandable impeller housing herein may include a distal portion as illustrated in exemplary FIG. 13A, and it may also include a proximal portion as illustrated in exemplary FIG. 13A.

The scaffolds herein may be manufactured using known techniques for creating stents or stent-like devices. For example, any of the scaffolds herein may be made by laser cutting a tubular member, such as a nitinol tubular member. Any description above related to manufacturing expandable scaffolds or expandable members is incorporated by reference into these embodiments.

FIG. 13B illustrates expandable impeller housing 552 of pump portion 550 from FIG. 13A before struts 556 are coupled to end region 559 of expandable blood conduit 554, and specifically, to scaffold 558. In this exemplary embodiment, pump portion 550 includes a first set of securing members 562, which in this embodiment are part of struts 556, and in this embodiment are each disposed at a first end region of struts 556 as shown. In this exemplary embodiment, pump portion 550 also includes a second set of securing members 563, which are each part of end region 559 of blood conduit 554, and are also part of the end region of scaffold 558. A first securing member 562 and a second securing member 563 are separately and together sized, positioned, and configured to engage one another such that one or more surfaces on each interact and cause a resistance to movement of one or both of the first and securing members in at least one direction. For example, when engaged, the first and/or second member may face resistance to movement in an axial direction (e.g., proximal and/or distal). Additionally, for example, when engaged the first and/or second member may face resistance to movement in a circumferential direction around the blood conduit (e.g., clockwise or counterclockwise in an end view of the impeller housing). Additionally, for example, when engaged the first and/or second member may face resistance to movement in a radial direction (e.g., radially outward or radially inward). Any first securing member and any second securing member herein may be separately and together sized, positioned, and configured to engage one another and thereby resist movement of one or both of the first and securing members in one or more of the aforementioned directions.

In this merely exemplary embodiment, second securing members 563 each comprise a bend formed in the scaffold, and may have valley configurations. In this embodiment, the bends are disposed at ends of scaffold 558, and in this embodiment there are four securing members 563, each of which is adapted and positioned to engage and interface with a first securing member 562 of a strut 556. In this exemplary embodiment, first securing members 562 may have a variety of configurations that are configured to interface with securing members 563 on scaffold 558. For example, securing members 562 may have "T" configurations in which the T shape fits through the space defined by the bend in the scaffold, and the lateral extensions of the "T" shape interface with the scaffold structure on either side of the bend in the scaffold. In another example is that first securing members 562 have comprise a bend or hook configuration that include a bend and then extend proximally towards their furthest end point. In these example, the hooks or bent regions may be passed through the scaffold opening from radially inward to radially outward, and the hook configuration hooks around the bend in the scaffold. In other embodiments the hooks may pass through the bends from radially outward to inward, and hook around the bend in the scaffold. During manufacture a force may optionally be applied to strut bends or hook to further secure the struts to the scaffold. Optionally, the struts may be further secured to the scaffold with a bond such as welding. Welding may optionally be used in combination with any mechanical interaction set forth herein to further secure a strut to a scaffold.

This disclosure also includes methods of manufacturing the pump portions herein, including any of the expandable impeller housings herein, including those that comprise one or more pluralities of struts that are non-unitary with blood conduit and scaffold end regions. The methods of manufacture may include attaching or securing one or more deformable layers of material (e.g., a membrane) to a scaffold which may comprise one or more scaffold sections, and forming a blood conduit. The methods may also include coupling a first plurality of struts to an end region of the blood conduit (such as to a scaffold) and optionally also coupling a second plurality of struts to a second end region of the blood conduit, such as an end region of a scaffold. For example, struts 556 in FIG. 13B may be coupled to scaffold 558, with the resulting coupling shown in FIG. 13A.

The methods of manufacture herein may also include securing an impeller to a drive mechanism, and positioning the impeller within the blood conduit, such as shown in FIGS. 13A and 13B. These methods of manufacturing may also include any other method of manufacturing step(s) described herein. One or more impellers may be positioned within a scaffold before the struts are coupled to the end region of the scaffold, such as is shown in FIG. 13B. FIG. 13B illustrates exemplary pump portion 550 after an impeller 560 and drive mechanism are positioned within scaffold 558 and before plurality of struts 556 have been coupled to the scaffold 558.

As mentioned above, an exemplary advantage of pump portions that include struts that are non-unitary with a blood conduit (including non-unitary with a scaffold thereof) is that struts may be made from different components or parts than the scaffold. This may provide for more design options and allow the struts to comprise a greater variety of materials and/or physical characteristics. For example without limitation, struts and scaffold sections that are not unitary may comprises different materials, they may have different stiffness, they may have different dimensions (e.g., radial thickness or circumferential "width") and/or it may be easier to configure the struts with a particular expanded configuration than if the struts and scaffold were unitary.

In some embodiments individual struts may have a stiffness that is greater than a stiffness of the end region of the scaffold from which they extend. The relative stiffness may be imparted or selected based on the material selection of the different components. In some embodiments, the relative stiffness may be in part due to relative dimensions of the struts and the scaffold. For example without limitation, struts may have a radial thickness (t) as illustrated in FIG. 13A that is greater than a radial thickness (t') of the scaffold in the end region from which the struts extend. Each of the plurality of struts may have a thickness t that is greater than a radial thickness of the scaffold, for example. Other dimensions of the relative components may also be varied based on the desired properties at any particular location. In some embodiments the struts may comprise a stiffer material than a scaffold material.

The expandable blood conduits herein may not comprise a metallic scaffold (e.g., nitinol scaffold), and the conduit is configured and adapted to define a blood lumen when expanded. In some of these embodiments the blood conduit comprises one or more polymeric materials that define a blood lumen, and radial support is provided by non-metallic structures, such as inflatable components and/or regions of increased polymeric stiffness. For example, the entire disclosure of WO2020028537A1 is incorporated by reference herein for all purposes, such as without limitation inflatable component(s) that are configured and adapted to provide radial support to the blood conduits therein. In these embodiments the struts may still be non-unitary with the expandable blood conduit. The disclosure thus includes struts that are not unitary with the blood conduit, even if the struts are not attached to a metallic scaffold. Additionally, blood conduits herein may include polymeric scaffolds, such as may be formed from polymeric materials. Struts (e.g., metallic, polymeric) may also be non-unitary with a blood conduit, including polymeric scaffolds, in these alternative examples.

The plurality of struts may comprise a material with a different chemical structure than a chemical structure of a scaffold material. That is, the type of material used for the struts may be different than the type of material used for the scaffold. For example, the struts may be made from nitinol, and the scaffold may be made from a different type of metal alloy, or vice versa. In any of the embodiments herein, struts may be made from the same material as the expandable scaffold (e.g., both made from Nitinol).

As shown in FIGS. 13A and 13B, proximal struts 556 may have a non-constant slope from a first end (e.g., proximal end) to a second end (e.g., distal end) of the struts. In this merely exemplary embodiment, a first section (which may be a proximal section or a distal section) of struts 556 has a constant or nearly constant slope as shown, and in an axially adjacent section (e.g. further distally or further distally) the slope increases, as shown, with a bend in between the two regions. The region of the struts closer to the expandable scaffold is, in this exemplary embodiment, more orthogonally oriented when expanded than the region of the struts axially further from the expandable scaffold, as shown. In other embodiments the slope of the struts in expanded configuration may be different than that in FIGS. 13A and 13B, such as constant or substantially constant along the length. The struts may have other configurations as well, such as other complex shapes.

A first region of any strut herein that is adjacent an expandable scaffold may be orthogonal, or substantially orthogonal, relative to a long axis of the expandable blood conduit. A second region axially further away from the expandable scaffold than the first region may have a configuration that is less orthogonally oriented, and optionally closer to parallel to the long axis (but not necessarily parallel), such as is shown in the struts in FIGS. 13A and 13B.

FIGS. 13A and 13B also illustrate a plurality of struts that may be formed unitarily with each other from a common starting structure. For example only, struts 556 may be formed starting with a tubular member 561, such as by laser cutting away material, to thereby create struts 556 with a first strut end extending from hub 561 and a second (free) end disposed away from the hub. The struts may be set in any desired expanded configuraiton, such as those shown in FIGS. 13A and 13B. The struts are configured to expand to the expanded configurations (e.g., such as shown in FIGS. 13A and 13B) when a radial constraint (such as from a delivery sheath) is removed, examples of which are described herein.

A drive mechanism for rotating one or more impellers may be disposed within and/or pass through strut hub 561. Any of the struts herein may be manufactured in this manner. Hub 561 is cylindrical in this example, but may have other outer profiles, such as rectilinear or curvilinear. Hub 561 includes a bore extending therethrough, allowing for a drive mechanism, and any number of bearings that facilitate the rotation of the one or more impellers. Hub 561 includes outer recesses in this embodiment, which are formed when the struts are formed and deformed radially away relative to the hub body.

FIGS. 13A and 13B may additionally illustrate struts that are coupled to end regions of scaffolds similar to those in FIGS. 3A-3D, 9 and 10, which may comprise scaffold sections that are disposed around an impeller. The non-unitary struts herein may be coupled to only one end region of either or both of the impeller scaffolds in FIGS. 3A-3D, 9 and 10, or non-unitary struts may be coupled to both end regions of either or both of the impeller scaffolds in FIGS. 3A-3D, 9 and 10. For example, in the examples in FIGS. 3A-3D, 9 and 10, there may be only one plurality of non-unitary struts, therey may be first and second pluralities of non-unitary struts, therey may be first, second and third pluralities of non-unitary struts, or there may be first, second, third and fourth pluralities of non-unitary struts. In some embodiments a proximal impeller scaffold may be coupled to a first plurality of non-unitary struts or to a first and second plurality of non-unitary struts. In some embodiments a distal impeller scaffold may be coupled to a first plurality of non-unitary struts or to a first and second plurality of non-unitary struts. Any of the pluralities of struts herein may thus be coupled, secured or attached to a scaffold or scaffold section in a non-unitary manner, which may provide any of the exemplary benefits provided herein.

It may be advantageous for the pump portion to have different properties or characteristics at different axially locations along the pump portion. In some embodiments it may be advantageous for the pump to have non-unitary struts at certain locations but not at others. For example, it may be advantageous to have struts at an outflow that are non-unitary with an end region of a scaffold near the outflow, but advantageous (or at least not disadvantageous) to have struts at an inflow of the pump that are unitary with a scaffold end region near the inflow of the pump portion. For example only, it may be advantageous to provide outflow struts with physical properties or characteristics, such as greater stiffness, but it may not be as advantageous or desired to have inflow struts with characteristics much different than an inflow end region of a scaffold. Pump portions herein may thus have unitary inflow struts and non-unitary outflow struts, or vice versa. Additionally, in embodiments such as in FIGS. 3A-3D, 9 and 10 with multiple impeller scaffold sections, it may be advantageous to include non-unitary struts at end regions of the blood conduit, and it may not be as advantageous or desired to have non-unitary struts at axially inner strut locations (which are within the blood conduit), or vice versa.

FIGS. 14A and 14B illustrate merely exemplary strut assemblies that includes a plurality of struts that are configured to be non-unitary with an end region of an expandable blood conduit. Many of the other pump components are not shown for clarity. FIG. 14A illustrates an exemplary strut assembly including a plurality of struts 622 (four are shown in this example). In this example each strut 622 has a first end extending from strut hub 621 towards a free end, as shown. Each of struts 622 includes a securing member 630 in a free end region as shown. Securing members 630 may be considered to provide similar functionality as securing members 562 in FIGS. 13A and 13B. Securing members 630 include an opening or space through the struts 622, as shown. Securing members 630 are configured, sized and positioned to interface with an end region of any of the scaffolds herein, wherein a portion of the scaffold regions extends at least partially within the opening or space in the strut 622. The securing members 630 of struts 622 include closed free ends 627, open regions 624 and 626, and interface or securing feature 625, which in this embodiment include first and second protrusions that extend from first and second side arm sections of struts 622. The side arms, protrusions 625 that extend therefrom, and closed end 627 at least partially define the opening or space in the strut 622 which is configured to a receive a scaffold section.

FIG. 14B illustrates an exemplary strut 622 from FIG. 14A coupled or secured to an end portion of an exemplary scaffold and is non-unitary with the end portion. FIG. 14B illustrates a merely exemplary coupling between non unitary struts and an end region of an expandable scaffold. In this example, the scaffold (only a very small poriton of which is shown) end region includes an elongate arm 643 that includes first and second protrusions 641 that extend outward from the elongate body of arm 643. In this embodiment first and second protrusions 641 extend laterally from arm body 643. Scaffold arms 643 (only one is shown) includes a first end 642 as well. Arm 643 extends at least partially within the opening or space in strut 622. In this example, protrusions 641 are sized and configured to interface with first and second side arms of strut 622 to help resist motion of at least one of the strut and arm 643 in at least one direction, described elsewhere herein. First end 642 of arm 643 is sized and configured to interface with a region of strut 622 to help secure the two components together as well.

To facilitate the coupling of scaffold arm 643 and strut 622, first and second side arms and securing features 625 (protrusions in this embodiment) of the strut may be moved apart from one another to increase the size of the opening or space in the strut. The end of arm 643 (which may be considered to have a "t" or "cross" configuration) may be advanced into the opening or space in the strut, which may occur along with some rotation of the arm 643 to case the insertion, until the interface features on the two components interface and couple the strut to the scaffold, thereby resisting movement of at least one of the strut and scaffold in at least one direction. A portion of the securing member 630 is therefore above the scaffold and a part of the securing member 630 is below the scaffold, as shown. A region of the strut axially overlaps with the end region of the scaffold, as shown. In the example in FIG. 14B, an end of the strut is further axially in one axial direction (e.g., proximally or distally) than an end of the scaffold end.

As can most easily seen in the top strut 622 in FIG. 14A, the securing members 630 may have a configuration in which the strut, at or just proximate to the opening in the strut, has a bends and follows a radially inward path towards the region where protrusions 625 extend from the side arms, after which the strut configuration follows a path that extends radially outward, forming a dip or valley in the region of the opening or space in the strut, as shown. The strut hubs herein may include rececesses 623 or 603 formed therein (only one is labeled in FIGS. 14A and 15) adjacent the struts. These may be formed by machining away material. Any aspect of any struts herein may be incorporated by reference into the examples shown in FIGS. 14A and 14B unless indicated herein to the contrary.

FIG. 15 illustrates an exemplary alternative strut assembly including a plurality of struts. The strut assembly in FIG. 15 may include any of the features and functionality of the strut assembly in FIGS. 14A and 14B. Parts that are similarly labeled in FIGS. 14A, 14B, and 15 may be the same and/or impart the same functionality as described with respect to FIGS. 14A and 14B. One difference between struts 602 shown in FIG. 15 is that securing members 610 have an open end 607, that may facilitate coupling with an end region of the scaffold, which is not shown but could be any of the scaffolds end regions herein, including scaffold arm 643 shown in FIG. 14B, for example. Upon coupling of struts 602 to an end region of the scaffold, an additional securing step may optionally be performed, such as applying force to the open end fingers 609 (labeled on only one strut) to crimp them together, for example, such that they contact each other in a closed configuration. Optionally, the fingers 609 shown at the strut free end may be welded together, creating a closed end of the strut.

The exemplary strut assemblies shown in FIGS. 14A, 14B and 15B may be disposed at a pump inflow or a pump outflow, and they may be proximal struts at a proximal end of the pump portion, distal struts at a distal end of the pump portion, and may be struts that are within the blood conduit, such as the struts in FIGS. 3A-3D that are within the blood conduit. A pump portion herein may thus have any combination of the strut assemblies herein at one or more locations of the pump portion. For example only, a pump portion may include the strut assembly in FIG. 14A at an outflow of an expandable impeller housing and may have unitary struts at an inflow of the expandable impeller housing.

What is claimed is:

1. A method of manufacturing a pump portion of a catheter blood pump, comprising:
   coupling each of a plurality of struts to an end region of an expandable scaffold, the expandable scaffold part of an expandable blood conduit that defines a blood lumen; and
   positioning one or more collapible impellers at least partially within the blood lumen.

2. The method of claim 1, further comprising securing a membrane to the expandable scaffold prior in time to the coupling step.

3. The method of claim 2, wherein securing a membrane to the expandable scaffold is performed on a mandrel.

4. The method of claim 1, further comprising coupling each of a second plurality of struts to a second end region of an expandable scaffold.

5. The method of claim 1, wherein the coupling step comprises coupling each of the plurality of struts that extend from a unitary hub to the end region of the expandable scaffold.

6. The method of claim 1, wherein positioning the one or more impellers occurs prior in time to coupling each of the plurality of struts to the end region of the expandable scaffold.

7. The method of claim 1, wherein the coupling step comprises coupling each of a plurality of struts to an end region of an expandable scaffold, wherein the expandable scaffold extends along the blood conduit.

8. The method of claim 1, wherein the coupling step comprises coupling each of a plurality of struts to a first scaffold section that is axially spaced from a second scaffold section.

9. The method of claim 8, further comprising coupling each of a second plurality of struts to the second scaffold section.

10. The method of claim 9, wherein coupling each of the second plurality of struts to the second end region of an expandable scaffold comprises coupling each of the second plurality of struts to a second scaffold section of the expandable scaffold.

11. The method of claim 1, wherein coupling each of a plurality of struts to an end region of an expandable scaffold comprises coupling each of a plurality of struts to an end region of an expandable scaffold from which a second plurality of struts extend, wherein the second plurality of struts are unitary with the scaffold.

12. The method of claim 11, wherein the second plurality of struts are unitary with a second scaffold section of the scaffold.

* * * * *